US012797453B2

(12) United States Patent
Milner et al.

(10) Patent No.: US 12,797,453 B2
(45) Date of Patent: Nov. 17, 2026

(54) LIPOSOME-BASED CANCER VACCINE COMPRISING A DISIALOGANGLIOSIDE (GD2 OR GD3), MONOPHOSPHORYL LIPID-A (MPL), AND CPG OLIGODEOXYNUCLEOTIDE (CPG-ODN)

(71) Applicant: University of Florida Research Foundation, Inc., Gainesville, FL (US)

(72) Inventors: Rowan Milner, Gainesville, FL (US); Elias Sayour, Gainesville, FL (US); Marc E. Salute, Gainesville, FL (US); Bikash Sahay, Gainesville, FL (US); Joanne Pigues Lagmay, Gainesville, FL (US); Mathew Cascio, Greenville, PA (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1239 days.

(21) Appl. No.: 17/429,196

(22) PCT Filed: Feb. 10, 2020

(86) PCT No.: PCT/US2020/017553
§ 371 (c)(1),
(2) Date: Aug. 6, 2021

(87) PCT Pub. No.: WO2020/163875
PCT Pub. Date: Aug. 13, 2020

(65) Prior Publication Data

US 2022/0133872 A1 May 5, 2022

Related U.S. Application Data

(60) Provisional application No. 62/803,103, filed on Feb. 8, 2019.

(51) Int. Cl.
*A61K 39/00* (2006.01)
*A61P 35/00* (2006.01)

(52) U.S. Cl.
CPC ...... *A61K 39/001171* (2018.08); *A61P 35/00* (2018.01); *A61K 2039/55555* (2013.01); *A61K 2039/55561* (2013.01); *A61K 2039/55566* (2013.01); *A61K 2039/55572* (2013.01); *A61K 2039/575* (2013.01)

(58) Field of Classification Search
CPC .. A61K 39/001171; A61K 2039/55555; A61K 2039/55561; A61K 2039/55572
See application file for complete search history.

(56) References Cited

U.S. PATENT DOCUMENTS

| | | | | |
|---|---|---|---|---|
| 4,235,871 A | | 11/1980 | Papahadjopoulos et al. | |
| 4,501,728 A | | 2/1985 | Geho et al. | |
| 4,837,028 A | | 6/1989 | Allen | |
| 4,877,611 A | | 10/1989 | Cantrell | |
| 5,019,369 A | | 5/1991 | Presant et al. | |
| 5,026,557 A | * | 6/1991 | Estis | A61K 9/1271 424/193.1 |
| 5,709,879 A | * | 1/1998 | Barchfeld | A61K 39/145 424/234.1 |
| 2005/0169929 A1 | | 8/2005 | Himmler et al. | |

FOREIGN PATENT DOCUMENTS

| | | |
|---|---|---|
| EP | 0381310 A1 | 8/1990 |
| WO | 02/92767 A2 | 11/2002 |
| WO | 2008/049643 A2 | 5/2008 |

OTHER PUBLICATIONS

Balamurugan, K., and P. Chintamani, 2018, Lipid nano particulate drug delivery: An overview of the emergmin trend, The Pharma Innovation J., 7(7):779-789.*
Milner, R. J., et al., 2006, The immune response to disialoganglioside GD3 vaccination in normal dogs: A melanoma surface antigen vaccine, Vet. Immunol. Immunopath. 114:273-284.*
Masso, O., et al., 1996, Specific Serological Response by Active Immunization with GD3-Bearing Liposomes, J. Pharmacol. Exp. Therap. 278(3):1114-1120.*
Smith, M. C., et al., 2017, Zeta potential: a case study of cationic, anionic, and neutral liposomes, Anal. Bioanal. Chem. 409:5779-5787.*
Zhao, Z., et al., 2018, Rational incorporation of molecular adjuvants into a hybrid nanoparticle-based nicotine vaccine for immunotherapy against nicotine addiction, Biomaterials 155:165-175, published online Nov. 20, 2017.*
Alexander et al., Development of an allogeneic whole-cell tumor vaccine expressing xenogeneic gp100 and its implementation in a phase II clinical trial in canine patients with malignant melanoma, Cancer Immunol. Immunother., 55(4):433-442 (2206).
Anagnostou et al., Evolution of Neoantigen Landscape during Immune Checkpoint Blockade in Non-Small Cell Lung Cancer, Cancer Discov., 7(3):264-276 (2016).
Andres et al., Increased levels of interleukins 8 and 10 as findings of canine inflammatory mammary cancer, Vet. Immunol. Immunopathol., 152:245-251 (2013).
Athanasiou et al., Magnitude of reactive thrombocytosis and associated clinical conditions in dogs, Vet. Rec., 181(10):267-267 (2017).
Ausubel et al., Current Protocols in Molecular Biology, Greene Publishing Associates (1992).

(Continued)

*Primary Examiner* — Jeffrey S Parkin
(74) *Attorney, Agent, or Firm* — MARSHALL, GERSTEIN & BORUN LLP

(57) ABSTRACT

A vaccine composition for enhancing in a subject to whom the composition is administered, a production of antibodies against a disialoganglioside GD3 and/or GD2 is provided in one embodiment. The composition includes, in an embodiment, a liposome including an effective amount of disialoganglioside GD3 and/or GD2 to stimulate or enhance antibody production in the subject; and an effective amount of an adjuvant comprising monophosphory 1 lipid A (MPL). In one example, the vaccine composition may be administered to the subject in conjunction with a chemotherapy.

16 Claims, 22 Drawing Sheets

Specification includes a Sequence Listing.

(56) References Cited

OTHER PUBLICATIONS

Baldridge et al., Monophosphoryl lipid A (Mpl) formulations for the next generation of vaccines, Methods, 19(1):103-107 (1999).
Banerjee et al., Modulating T regulatory cells in cancer: how close are we?, Immunol. Cell. Biol., 91(5):340-349 (2013).
Bergman et al., Long-Term Survival of Dogs with Advanced Malignant Melanoma after DNA Vaccination with Xenogeneic Human Tyrosinase: A Phase I Trial, Clin. Cancer Res., 9(4):1284-1290 (2003).
Boston et al., Efficacy of systemic adjuvant therapies administered to dogs after excision of oral malignant melanomas: 151 cases (2001-2012), J. Am. Vet. Med. Assoc., 245(4):401-407 (2014).
Brodersen et al., Analysis of the immunological cross reactivities of 213 well characterized monoclonal antibodies with specificities against various leucocyte surface antigens of human and 11 animal species, Vet. Immunol. Immunopathol., 64(1):1-13 (1998).
Bronte et al., Recommendations for myeloid-derived suppressor cell nomenclature and characterization standards, Nat. Commun., 7:12150 (2016).
Brusa et al., Circulating immunosuppressive cells of prostate cancer patients before and after radical prostatectomy: Profile comparison, Int. J. Ural., 20:971-978 (2013).
Calvalido et al., Comparison of serum cytokine levels between dogs with multicentric lymphoma and healthy dogs, Vet. Immunol. Immunopathol., 182:106-114 (2016).
Chang et al., CCL2 Produced by the Glioma Microenvironment Is Essential for the Recruitment of Regulatory T Cells and Myeloid-Derived Suppressor Cells, Cancer Res., 76(19):5671-5682 (2016).
Cheever et al., The prioritization of cancer antigens: a national cancer institute pilot project for the acceleration of translational research, Clin. Cancer Res., 15(17):5323-5337 (2009).
Cheresh et al., Disialoganglioside GD3 on human melanoma serves as a relevant target antigen for monoclonal antibody-mediated tumor cytolysis, Proc. Natl. Acad. Sci. USA., 82(15):5155-5159 (1985).
Chibowski et al., Zeta potential and surface charge of DPPC and DOPC liposomes in the presence of PLC enzyme, Adsorption, 22:755-765 (2016).
Chun et al., CCL2 Promotes Colorectal Carcinogenesis by Enhancing Polymorphonuclear Myeloid-Derived Suppressor Cell Population and Function, Cell. Rep., 12(2):244-257 (2015).
Conti et al., CCL2 (monocyte chemoattractant protein-1) and cancer, Semin. Cancer Biol., 14(3):149-154 (2004).
Damuzzo et al., Complexity and challenges in defining myeloid-derived suppressor cells, Cytometry B Clin. Cytom., 88:77-91 (2015).
Dobrenkov et al., Oncotargets GD2 and GD3 are highly expressed in sarcomas of children, adolescents, and young adults, Pediatr Blood Cancer, 63(10):1780-1785 (2016).
Dolcetti et al., Hierarchy of immunosuppressive strength among myeloid-derived suppressor cell subsets is determined by GM-CSF, Eur. J. Immunol., 40(1):22-35 (2009).
Dow et al., In vivo tumor transfection with superantigen plus cytokine genes induces tumor regression and prolongs survival in dogs with malignant melanoma, J. Clin. Invest., 101(11):2406-2414 (1998).
Draxler et al., A flowcytometric analysis to efficiently quantify multiple innate immune cells and T Cell subsets in human blood, Cytom. Part J. Int. Soc. Anal. Cytol., 91(4):336-350 (2017).
Duffy et al., Comparative analysis of monocytic and granulocytic myeloid-derived suppressor cell subsets in patients with gastrointestinal malignancies, Cancer Immunol. Immunother., 62:299-307 (2013).
Euler et al., Efficient adenovector CD40 ligand immunotherapy of canine malignant melanoma, J. Immunother., 31(4):377-384 (2008).
Finocchiaro et al., Cytokine-Enhanced Vaccine and Interferon-β plus Suicide Gene Therapy as Surgery Adjuvant Treatments for Spontaneous Canine Melanoma, Hum. Gene. Ther., 26(6):367-376 (2015).
Florcken et al., Myeloid-derived suppressor cells in human peripheral blood: Optimized quantification in healthy donors and patients with metastatic renal cell carcinoma, Immunol. Lett., 168(2):260-267 (2015).
Gabrilovich et al., Coordinated regulation of myeloid cells by tumours, Nat. Rev. Immunol., 12:253-268 (2012).
Gabrilovich et al., Myeloid-derived suppressor cells as regulators of the immune system, Nat. Rev. Immunol., 9:162-174 (2009).
Gillard et al., Naturally occurring melanomas in dogs as models for non-UV pathways of human melanomas, Pigment Cell Melanoma Res., 27(1):90-102 (2014).
Goulart et al., Identification of Myeloid Derived Suppressor Cells in Dogs with Naturally Occurring Cancer, PLoS ONE, 7(3):e33274 (2012).
Goulart et al., Phenotypic and transcriptomic characterization of canine myeloid-derived suppressor cells, Sci. Rep., 9(1):3574 (2019).
Helfand et al., GD3 ganglioside antibody augments tumoricidal capacity of canine blood mononuclear cells by induction of interleukin 12, Cancer Res., 59(13):3119-3127 (1999).
Helfand et al., Induction Of Lymphokine-Activated Killer (LAK) Activity in Canine Lymphocytes with Low Dose Human Recombinant Interleukin-2 in vitro, Cancer Biother., 9(3):237-244 (1994).
Hernandez et al., Naturally Occurring Canine Melanoma as a Predictive Comparative Oncology Model for Human Mucosal and Other Triple Wild-Type Melanomas, Int. J. Mol. Sci., 19(2):394 (2018).
Hogge et al., Preclinical development of human granulocyte-macrophage colonystimulating factor-transfected melanoma cell vaccine using established canine cell lines and normal dogs, Cancer Gene. Ther., 6:26-36 (1999).
Huang et al., CCL2/CCR2 pathway mediates recruitment of myeloid suppressor cells to cancers, Cancer Lett., 252(1):86-92 (2007).
International Application No. PCT/US20/17553, International Preliminary Report on Patentability, mailed Aug. 19, 2021.
International Application No. PCT/US20/17553, International Search Report and Written Opinion, mailed Jun. 16, 2020.
Invivogen, "Vaccine Adjuvants"; Publication [online]. 2011 Retrieved from the Internet: <URL: https://www.invivogen.com/review-vaccine-adjuvants>; pp. 1-3.
Ishioka et al., Monocyte Chemoattractant Protein-1 in Dogs Affected with Neoplasia or Inflammation, J. Vet. Med. Sci., 75(2):173-177 (2013).
Jacobsen et al., Reactivities of 20 anti-human monoclonal antibodies with leucocytes from ten different animal species, Vet. Immunol. Immunopathol., 39(4):461-466 (1993).
James et al., CpG-mediated modulation of MDSC contributes to the efficacy of Ad5-TRAIL therapy against renal cell carcinoma, Cancer Immunol. Immunother., 63(11):1213-1227 (2014).
Jiang et al., Elevated chronic inflammatory factors and myeloid-derived suppressor cells indicate poor prognosis in advanced melanoma patients, Int. J. Cancer, 136(10):2352-2360 (2015).
Jiang et al., Phenotypes, accumulation, and functions of myeloid-derived suppressor cells and associated treatment strategies in cancer patients, Hum. Immunol., 75(11):1128-1137 (2014).
Jordan et al., Myeloid-derived suppressor cells are associated with disease progression and decreased overall survival in advanced-stage melanoma patients, Cancer Immunol. Immunother., 62(11):1711-1722 (2013).
Khaled et al., Myeloid-derived suppressor cells in cancer: recent progress and prospects, Immunol. Cell. Biol., 91(8):493-502 (2013).
Kim et al., Association of Serum and Intratumoral Cytokine Profiles with Tumor Stage and Neutrophil Lymphocyte Ratio in Colorectal Cancer, Anticancer Res., 34(7):3481-3487 (2014).
Lana et al., Diagnosis of Mediastinal Masses in Dogs by Flow Cytometry, J. Vet. Intern. Med., 20(5):1161-1165 (2006).
Zoglmeier et al., CpG blocks immunosuppression by myeloid-derived suppressor cells in tumor-bearing mice, Clin. Cancer Res., 17(7):1765-1775 (2011).
Lechner et al., Characterization of Cytokine-Induced Myeloid-Derived Suppressor Cells from Normal Human Peripheral Blood Mononuclear Cells, J. Immunol., 185(4):2273-2284 (2010).
Lim et al., Targeting the CCL2-CCR2 signaling axis in cancer metastasis, Oncotarget, 7(19):28697-28710 (2016).

(56) References Cited

OTHER PUBLICATIONS

Lindsay et al., Blinded by the light: why the treatment of metastatic melanoma has created a new paradigm for the management of cancer, Ther. Adv. Med. Oncol., 7(12):107-121 (2012).
Lopez et al., Gangliosides in cell recognition and membrane protein regulation, Curr. Opin. Struct. Biol., 19(5):549-557 (2009).
Macewen et al., Adjuvant therapy for melanoma in dogs: results of randomized clinical trials using surgery, liposome-encapsulated muramyl tripeptide, and granulocyte macrophage colony-stimulating factor, Clin. Cancer Res., 5(12):4249-4258 (1999).
Macewen et al., Canine oral melanoma: comparison of surgery versus surgery plus Corynebacterium parvum, Cancer Invest., 4(5):397-402 (1986).
Mandruzzato et al., Toward harmonized phenotyping of human myeloid-derived suppressor cells by flow cytometry: results from an interim study, Cancer Immunol. Immunother., 65:161-169 (2016).
Manley et al., Xenogeneic Murine Tyrosinase DNA Vaccine for Malignant Melanoma of the Digit of Dogs, J. Vet. Intern. Med., 25(1):94-99 (2011).
Marvel et al., Myeloid-derived suppressor cells in the tumor microenvironment: expect the unexpected, J. Clin. Invest., 125(9):3356-3364 (2015).
Meyer et al., Frequencies of circulating MDSC correlate with clinical outcome of melanoma patients treated with ipilimumab, Cancer Immunol. Immunother., 63:247-257 (2014).
Milner et al., Abstract A29: Differential expression of the gangliosides GD3 and GD2 in canine and human osteosarcoma cell lines: An immunotherapy target, Cancer Immunol. Res., 3:A29-A29 (2015).
Milner et al., The immune response to disialoganglioside GD3 vaccination in normal dogs: a melanoma surface antigen vaccine, Vet. Immunol. Immunopathol., 114:273-284 (2006).
Mucha et al., MDSCs Mediate Angiogenesis and Predispose Canine Mammary Tumor Cells for Metastasis via IL-28/IL-28RA (IFN-lambda) Signaling, PLoS ONE, 9:e103249 (2014).
Neel et al., Thrombocytosis: a retrospective study of 165 dogs, Vet. Clin. Pathol., 41(2):216-222 (2012).
O'Neill et al., Changes in Regulatory T Cells in Dogs with Cancer and Associations with Tumor Type, J. Vet. Intern. Med., 23(4):875-881 (2009).
Owen, TNM Classification of Tumours in Domestic Animals, (1980).
Paolo et al., Neuroblastoma-targeted Nanoparticles Entrapping siRNA Specifically Knockdown ALK, Molecular Therapy, 19(6): 1131-1140 (2011).
Park et al., Fine specificity of natural killer T cells against GD3 ganglioside and identification of GM3 as an inhibitory natural killer T-cell ligand, Immunology, 123(1):145-155 (2008).
Perrie et al., Designing liposomal adjuvants for the next generation of vaccines, Adv. Drug. Deliv. Rev., 99:85-96 (2016).
Perrie et al., Manufacturing Methods for Liposome Adjuvants, Methods Mol. Biol., 1494:127-144 (2017).
Perry et al., Increased monocyte chemotactic protein-1 concentration and monocyte count independently associate with a poor prognosis in dogs with lymphoma, Vet. Comp. Oncol., 9(1):55-64 (2011).
Popa et al., GD3-replica peptides selected from a phage peptide library induce a GD3 ganglioside antibody response, Federation of European Biochemical Societies Letters, 580(5):1398-1404 (2006).
Rao et al., Class II Major Histocompatibility Complex Expression and Cell Size Independently Predict Survival in Canine B-Cell Lymphoma, J. Vet. Intern. Med., 25:1097-1105 (2011).
Rowan et al., Abstract A204: A protective GD3-based vaccine increases NKT-cells in a C57BL/6 murine model, Cancer Immunol. Res., 7:(2_Supplement): A204 (2019).
Rudolph et al., Increased frequencies of CD11b+CD33+CD14+ HLA-DRlow myeloid-derived suppressor cells are an early event in melanoma patients, Exp. Dermatol., 23(3):202-204 (2014).
Sambrook et al., Molecular Cloning: A Laboratory Manual, 2nd Edition, Cold Spring Harbor, New York (1989).
Sanctis et al., MDSCs in cancer: Conceiving new prognostic and therapeutic targets, Biochim. Biophys. Acta., 1865(1):35-48 (2016).
Schiffman et al., Comparative oncology: what dogs and other species can teach us about humans with cancer, Philos. Trans. R. Soc. B Biol. Sci., 370:20140231 (2015).
Schilling et al., Vemurafenib reverses immunosuppression by myeloid derived suppressor cells, Int. J. Cancer, 133(7):1653-1663 (2013).
Schmidt et al., Elevated neutrophil and monocyte counts in peripheral blood are associated with poor survival in patients with metastatic melanoma: a prognostic model, Br. J. Cancer., 93:273-278 (2005).
Sherger et al., Identification of myeloid derived suppressor cells in the peripheral blood of tumor bearing dogs, BMC Vet. Res., 8:209 (2012).
Shirota et al., Intratumoral Injection of CpG Oligonucleotides Induces the Differentiation and Reduces the Immunosuppressive Activity of Myeloid-Derived Suppressor Cells, J. Immunol., 188(4):1592-1599 (2012).
Simpson et al., Sporadic naturally occurring melanoma in dogs as a preclinical model for human melanoma, Pigment Cell Melanoma Res., 27(1):37-47 (2014).
Skorupski et al., Carboplatin versus alternating carboplatin and doxorubicin for the adjuvant treatment of canine appendicular osteosarcoma: a randomized, phase III trial, Vet. Comp. Oncol., 14(1):81-87 (2016).
Smedley et al., Prognostic Markers for Canine Melanocytic Neoplasms: A Comparative Review of the Literature and Goals for Future Investigation, Vet. Pathol., 48(1):54-72 (2011).
Sottnik et al., Association of Blood Monocyte and Lymphocyte Count and Disease-Free Interval in Dogs with Osteosarcoma, J. Vet. Intern. Med., 24(6):1439-1444 (2010).
Szoka et al., Comparative Properties and Methods of Preparation of Lipid Vesicles (Liposomes), Ann. Rev. Biophys. Bioeng., 9:467-508 (1980).
Tcyganov et al., Plasticity of myeloid-derived suppressor cells in cancer, Curr. Opin. Immunol., 51:76-82 (2018).
Tikoo et al., Friends or foes: IL-10 and TGF-P in melanoma, Exp. Dermatol., 24(4):254-255 (2015).
Tsai et al., Tumor Microenvironment: A New Treatment Target for Cancer, ISRN Biochem., 2014:1-8 (2014).
Vasievich et al., The suppressive tumor microenvironment: a challenge in cancer immunotherapy, Mol. Pharm., 8(3):635-641 (2011).
Vesely et al., Natural Innate and Adaptive Immunity to Cancer, Annu. Rev. Immunol., 29:235-271 (2011).
Watanabe et al., Small interfering RNA (siRNA) against the Bcl-2 gene increases apoptosis in a canine melanoma cell line, J. Vet. Med. Sci., 72(3):383-386 (2010).
Williams et al., Association between lymph node size and metastasis in dogs with oral malignant melanoma: 100 cases (1987-2001), J. Am. Vet. Med. Assoc., 222(9):1234-1236 (2003).
Wong et al., Cross-species genomic landscape comparison of human mucosal melanoma with canine oral and equine melanoma, Nat. Commun., 10:353 (2019).
Yamauchi et al., Circulating and Tumor Myeloid-derived Suppressor Cells in Resectable Non-Small Cell Lung Cancer, Am. J. Respir. Crit. Care Med., 198(6):777-787 (2018).
Yao et al., IL-10-Producing Lymphocytes in Inflammatory Disease, Int. Rev. Immunol., 32(3):324-336 (2013).
Yuan et al., Pre- and post-operative evaluation: percentages of circulating myeloid-derived suppressor cells in rectal cancer patients, Neoplasma, 62(2):239-249 (2015).
Zhang et al., CC chemokine ligand 2 (CCL2) promotes prostate cancer tumorigenesis and metastasis, Cytokine Growth Factor Rev., 21(1):41-48 (2010).
Zhao et al., Phenotype, development, and biological function of myeloid-derived suppressor cells, Oncoimmunology, 5(2):e1004983 (2016).

* cited by examiner

Figure 1: Malvern NanoSight NS300 results showing uniform distribution of the nano-liposomal particles in the MPL emulsion.

Figure 2: Cryo-electron microscopy of the nano-liposomal particles in the MPL emulsion showing the bi-lipid characteristic of the liposome (small box).

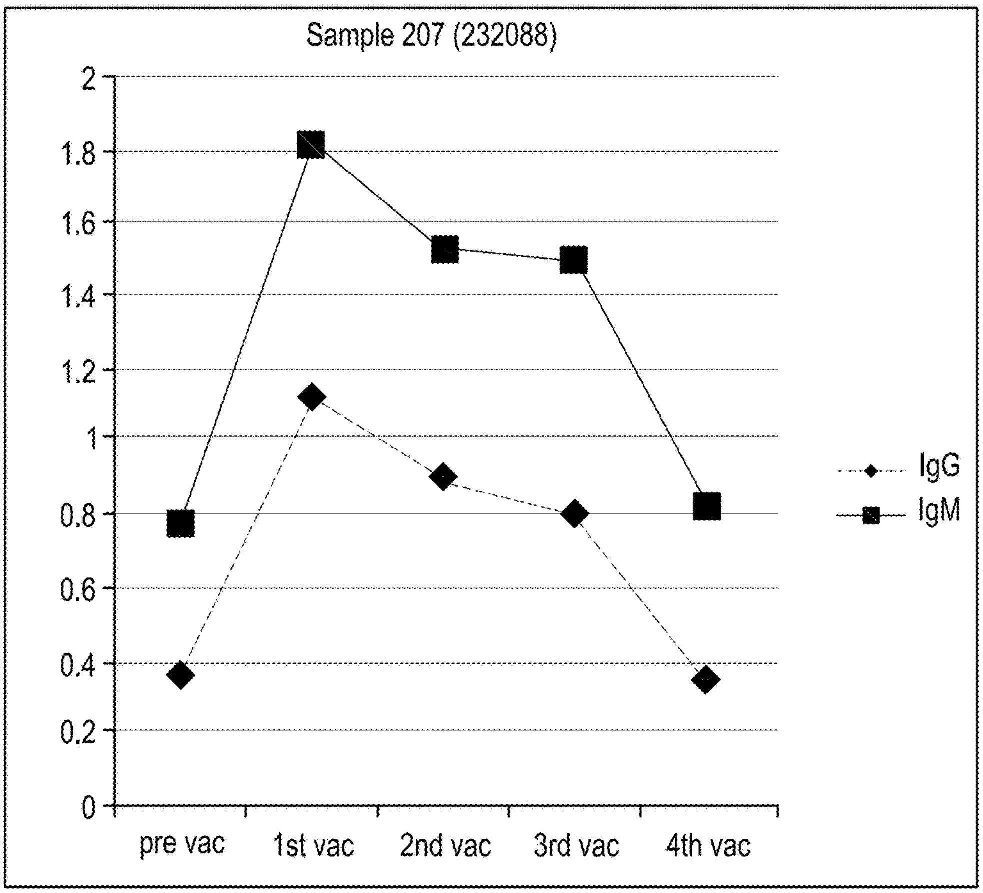
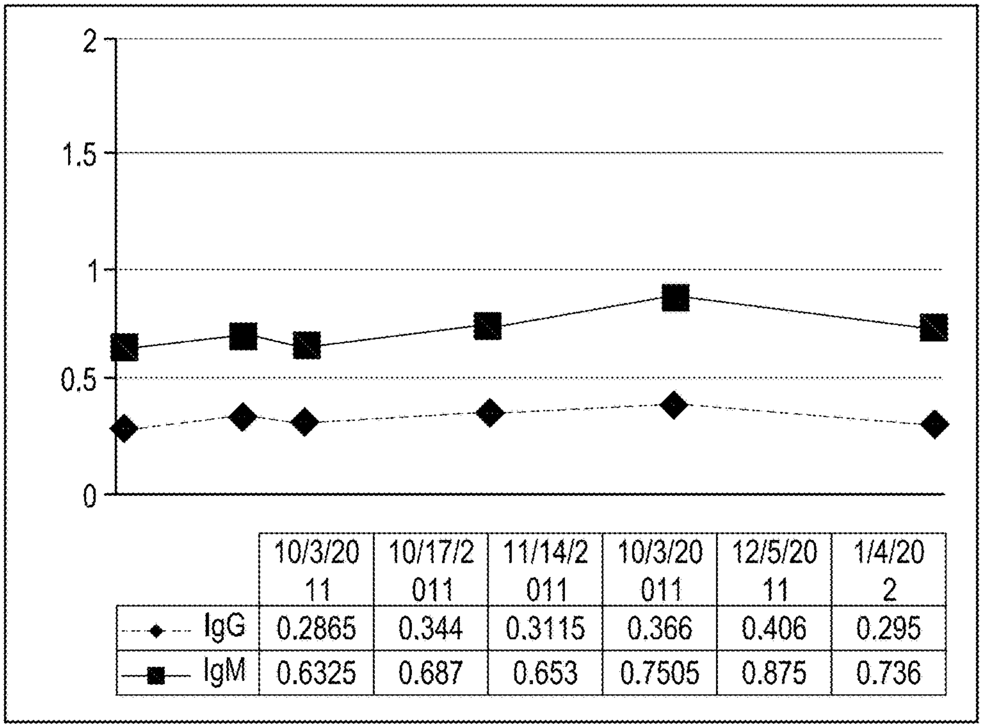
| | 10/3/2011 | 10/17/2011 | 11/14/2011 | 10/3/2011 | 12/5/2011 | 1/4/202 |
|---|---|---|---|---|---|---|
| IgG | 0.2865 | 0.344 | 0.3115 | 0.366 | 0.406 | 0.295 |
| IgM | 0.6325 | 0.687 | 0.653 | 0.7505 | 0.875 | 0.736 |
FIG. 3

Melanoma GD3 Dogs Vaccinated over 4 months
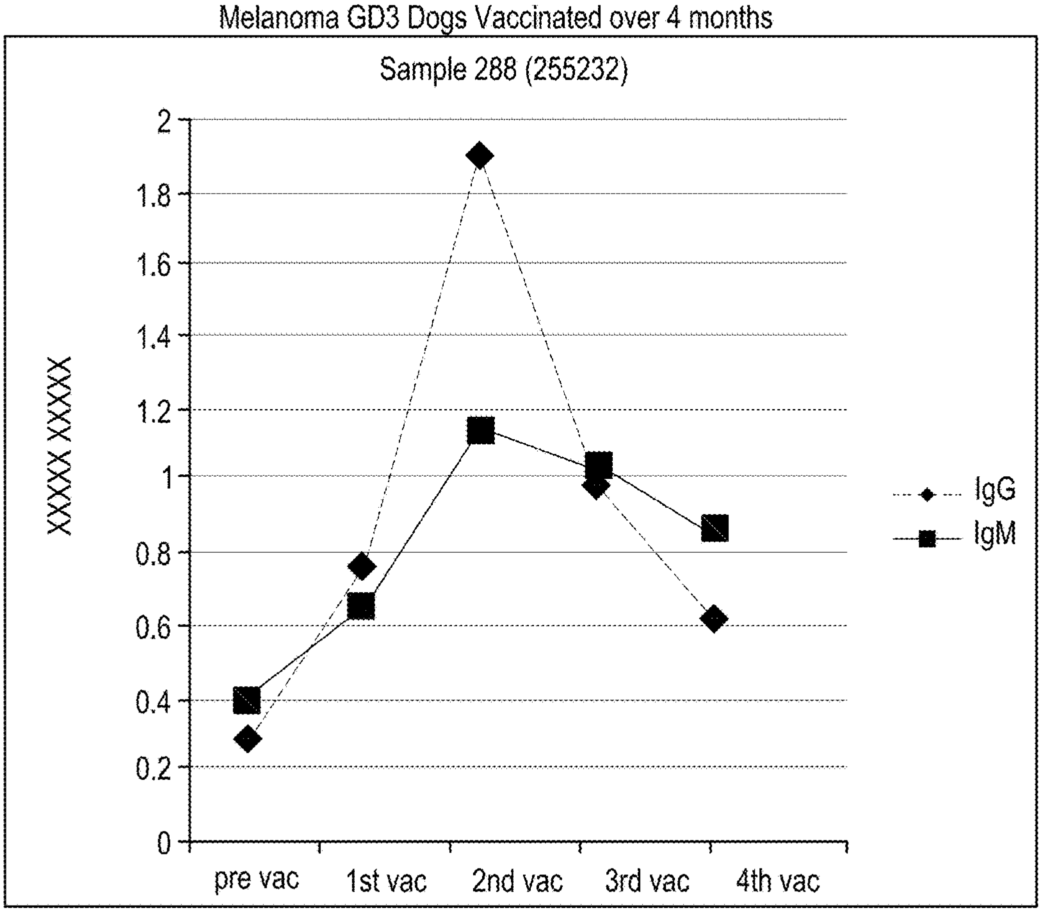
Normal control dogs-vaccinated with PBS over 4 months
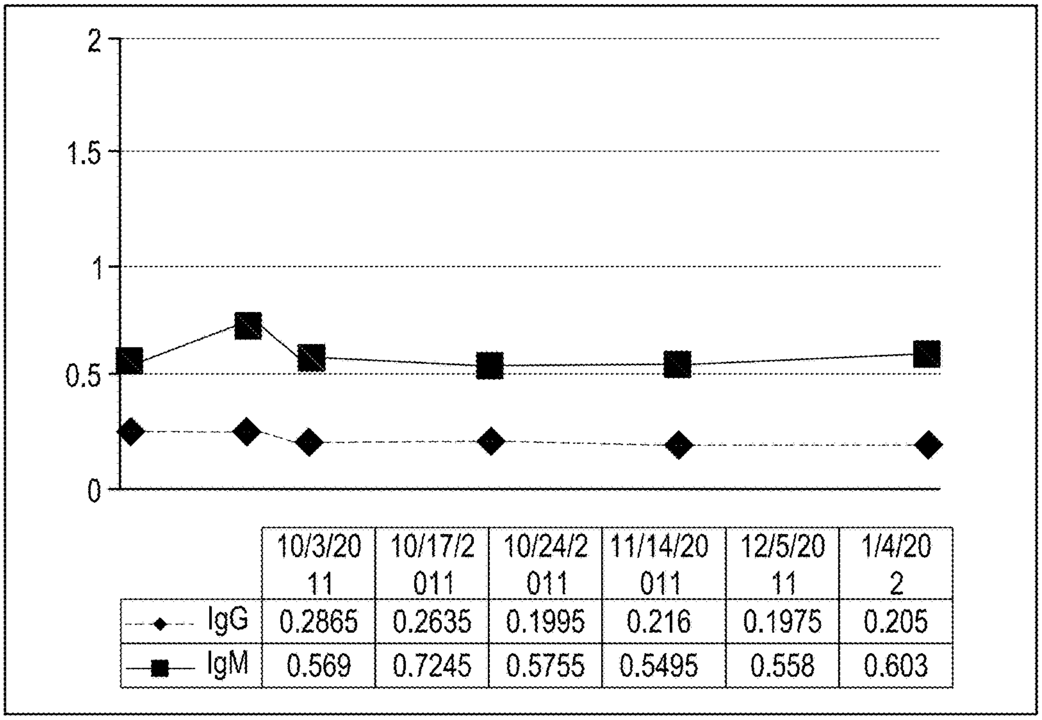
| | 10/3/2011 | 10/17/2011 | 10/24/2011 | 11/14/2011 | 12/5/2011 | 1/4/2012 |
|---|---|---|---|---|---|---|
| IgG | 0.2865 | 0.2635 | 0.1995 | 0.216 | 0.1975 | 0.205 |
| IgM | 0.569 | 0.7245 | 0.5755 | 0.5495 | 0.558 | 0.603 |
FIG. 3(Continued)

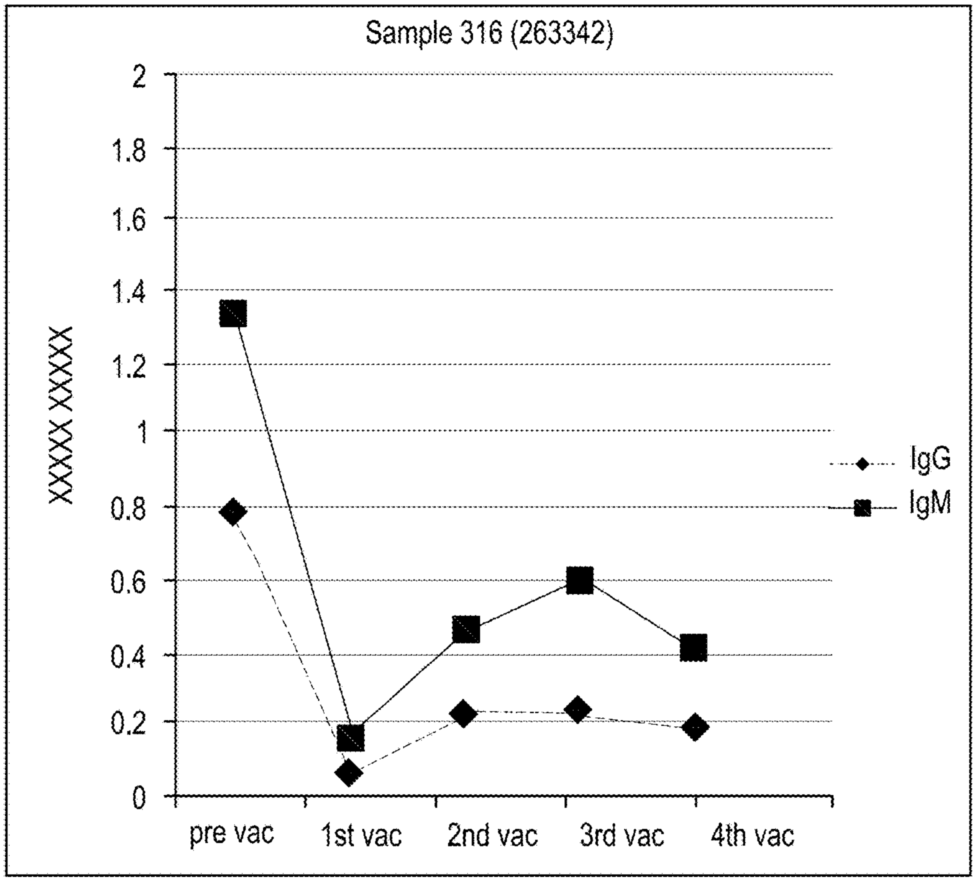
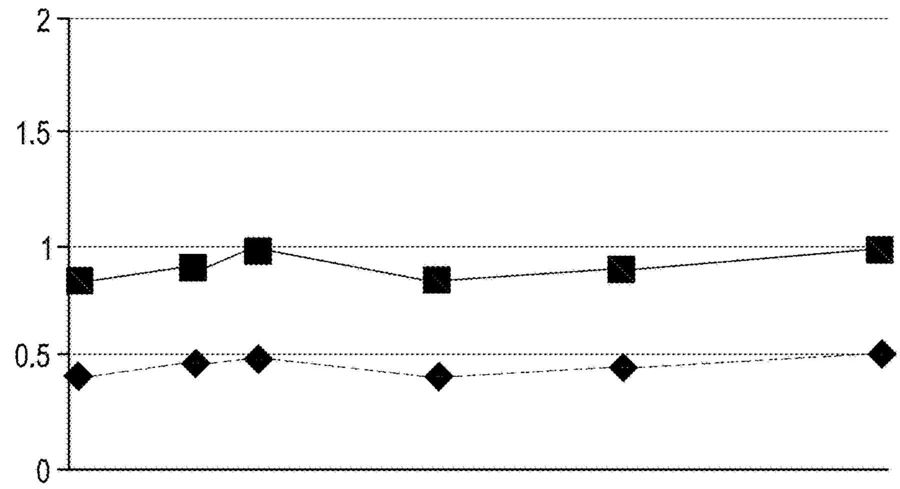
| | 10/3/2011 | 10/24/2011 | 11/14/2011 | 10/3/2011 | 12/5/2011 | 1/4/202 |
|---|---|---|---|---|---|---|
| IgG | 0.4055 | 0.461 | 0.505 | 0.3875 | 0.441 | 0.5005 |
| IgM | 0.816 | 0.8805 | 0.9405 | 0.825 | 0.8765 | 0.9665 |
FIG. 3(Continued)

DFI DATA

| Vaccine Group | Survival Time | Std. Error | 95% Conf. Lower | 95% Conf. Upper |
|---|---|---|---|---|
| Mean | 719.694 | 123.177 | 478.272 | 961.117 |
| 25th % | -- | -- | -- | -- |
| 50 (Median) | 360.000 | (+inf) | (-inf) | (+inf) |
| 75th % | 197.000 | 52.765 | 93.583 | 300.417 |

| Control Group | Survival Time | Std. Error | 95% Conf. Lower | 95% Conf. Upper |
|---|---|---|---|---|
| Mean | 587.177 | 122.605 | 366.476 | 807.879 |
| 25th % | 792.000 | 122.648 | 551.614 | 1032.386 |
| 50 (Median) | 463.000 | 236.634 | -0.793 | 926.739 |
| 75th % | 160.000 | 30.734 | 99.762 | 220.238 |

| Data Summary | Total | Missing | Events | Censored | Percent Censored | Median Time |
|---|---|---|---|---|---|---|
| Vaccine Group | 25 | 0 | 11 | 14 | 56 | 360 |
| Control Group | 30 | 0 | 21 | 9 | 30 | 463 |
| Overall | 55 | 0 | 32 | 23 | 42 | |

FIG. 7

OVERALL SURVIVAL

| Vaccine Group | Survival Time | Std. Error | 95% Conf. Lower | 95% Conf. Upper |
|---|---|---|---|---|
| Mean | 750.733 | 114.597 | 526.127 | 975.339 |
| 25th % | -- | -- | -- | -- |
| 50 (Median) | 551.000 | (+inf) | (-inf) | (+inf) |
| 75th % | 221.000 | 62.041 | 99.402 | 342.598 |

| Control Group | Survival Time | Std. Error | 95% Conf. Lower | 95% Conf. Upper |
|---|---|---|---|---|
| Mean | 770.993 | 139.922 | 496.750 | 1045.235 |
| 25th % | -- | -- | -- | -- |
| 50 (Median) | 479.000 | 233.014 | 22.301 | 935.699 |
| 75th % | 174.000 | 43.000 | 89.722 | 258.278 |

| Data Summary | Total | Missing | Events | Censored | Percent Censored | Median Time |
|---|---|---|---|---|---|---|
| Vaccine Group | 25 | 0 | 11 | 14 | 56 | 551 |
| Control Group | 30 | 0 | 18 | 12 | 40 | 479 |
| Overall | 55 | 0 | 29 | 26 | 47 | |

FIG. 9

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Asp Pro Ser His Ser Leu Gly Leu Asp Ala Ala Leu Phe Met
1               5                   10                  15


<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Cys Asn Pro Asn Met Glu Pro Pro Arg Cys Trp Ala Ala Glu Gly
1               5                   10                  15

Asp


<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg His Ala Tyr Arg Ser Met Ala Glu Trp Gly Phe Leu Tyr Ser
1               5                   10                  15


<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

tcgtcgttgt cgttttgtcg tt                                              22
```

LIPOSOME-BASED CANCER VACCINE COMPRISING A DISIALOGANGLIOSIDE (GD2 OR GD3), MONOPHOSPHORYL LIPID-A (MPL), AND CPG OLIGODEOXYNUCLEOTIDE (CPG-ODN)

CROSS REFERENCE TO RELATED APPLICATIONS AND INCORPORATION BY REFERENCE OF MATERIAL SUBMITTED ELECTRONICALLY

This application is a U.S. national stage of International Application No. PCT/US2020/017553, filed Feb. 10, 2020, which claims the benefit of U.S. Provisional Patent Application No. 62/803,102, filed Feb. 8, 2019, the entire contents of each of which are fully incorporated herein by reference.

The instant application contains a Sequence Listing which has been submitted electronically in ASCII format and is hereby incorporated by reference in its entirety. Said ASCII copy, created on Jul. 21, 2021, is named 3291726301US_SL.txt and is 1,418 bytes in size.

BACKGROUND

Cancer has an ability to evade destruction by the immune system, yet evidence of immunosurveillance and immunoediting of cancerous cells suggests that efficient and effective cancer therapies may be attainable by informed manipulation of the immune system. Results of such approaches to date have been inconclusive, due in part to the complexity and still limited understanding of many features of cancer and the immune system, including such features as exhaustion of tumor-reactive T cell populations, immunosuppression by regulatory T cells in tumors, mutability of tumor antigens, and the like.

Disialoganglioside GD3 represents a major surface marker on most human melanoma cells. Monoclonal antibodies directed to GD3 have been used to recognize GD3 and effectively lyse four human melanoma cell lines expressing significant levels of GD3 on their surface by either of two mechanisms: 1) antibody-dependent cellular cytotoxicity (ADCC) or 2) complement-mediated cytotoxicity. However, a melanoma cell line that expresses minimal levels of GD3 on 13% of the cells has shown insignificant lysis by monoclonal antibodies by either of these two mechanisms, suggesting that a threshold level of antigen expression may be required for effective in vitro cytolysis.

Given the poor prognosis of melanoma and osteosarcoma cancers, novel therapeutic approaches are needed to improve survival. Chemotherapy is only marginally effective as a treatment modality, and causes numerous side effects, while other modalities such as immunotherapy are still in their infancy. Cancer vaccines are designed to elicit an immune response against tumor-specific or tumor-associated antigens, encouraging the immune system to attack cancer cells bearing these antigens. However, development of cancer vaccines is challenging due to on-going clonal evolution in the cancer cell population which frequently modifies the target epitopes of the cancer vaccines. Moreover, uptake of the vaccine and timing of vaccine delivery limits the effectivity of this immunotherapeutic approach to cancer treatment.

Adoptive T-cell therapies are used for immunotherapies for the treatment of various cancers; however, these treatments include live whole cells, and must be administered after chemotherapy. In some instances it would be beneficial to couple chemotherapy with other therapies, including immunotherapy, simultaneously as opposed to providing these therapies in sequence.

SUMMARY

A different and novel approach to cancer vaccines is provided in embodiments described herein, including, for example, a nanoliposome including a GD3 antigen, a GD2 antigen, or a combination thereof, and an adjuvant for treating or preventing cancer in a subject. In one embodiment, the adjuvant includes monophospholipid A (MPL) as a primary constituent of the nanoliposome to initiate an immune response significant enough to overcome any tolerances in the subject, for example.

In an embodiment, a vaccine composition for enhancing production of antibodies against disaloganglioside GD3 and/or GD2 is provided. The vaccine composition includes an admixture of an effective amount of disialoganglioside GD3 and/or GD2 to enhance antibody production in a subject, and an effective amount of an adjuvant comprising monophosphoryl lipid A (MPL).

In another embodiment, a method of treating a cancer in a subject is provided including vaccinating a subject by administering to the subject an effective amount of the vaccine composition described herein, wherein the vaccine composition is effective to produce antibodies against disialoganglioside GD3 or GD2, or both.

In yet another embodiment, a method of producing a GD3 and/or GD2-containing nano-liposomes, is provided. The method includes combining an effective amount of a disialoganglioside GD3 self-antigen and/or GD2 self-antigen, and an effective amount of a monophospohoryl lipid A (MPL) (a "first composition"), and subjecting the first composition to sonication to produce an emulsified first composition ("emulsified composition").

BRIEF DESCRIPTION OF THE DRAWINGS

FIG. 3 provides graphical illustrations of IgG and IgM specific immune response to GD3 vaccination in dogs with melanoma and in normal dogs.

FIG. 7 is a chart showing the data for the DFI graph in the osteosarcoma vaccine trial.

FIG. 9 is a chart showing the data displayed in the overall survival rate graph in FIG. 8.

(FIG. 15A) A representative dot plot shows an increase in NKT cells in liver but not in blood and spleen (data not shown). (FIG. 15B) A compiled NKT cells data showing a significant increase in the liver of vaccinated mice. n=4, *<P0.05, **<P0.01.

(FIG. 16B) Tumor size in male mice and (FIG. 16C) Tumor size in female mice. n=5, *<P0.05, ****<P0.0001

DETAILED DESCRIPTION

Definitions

Figure 1:
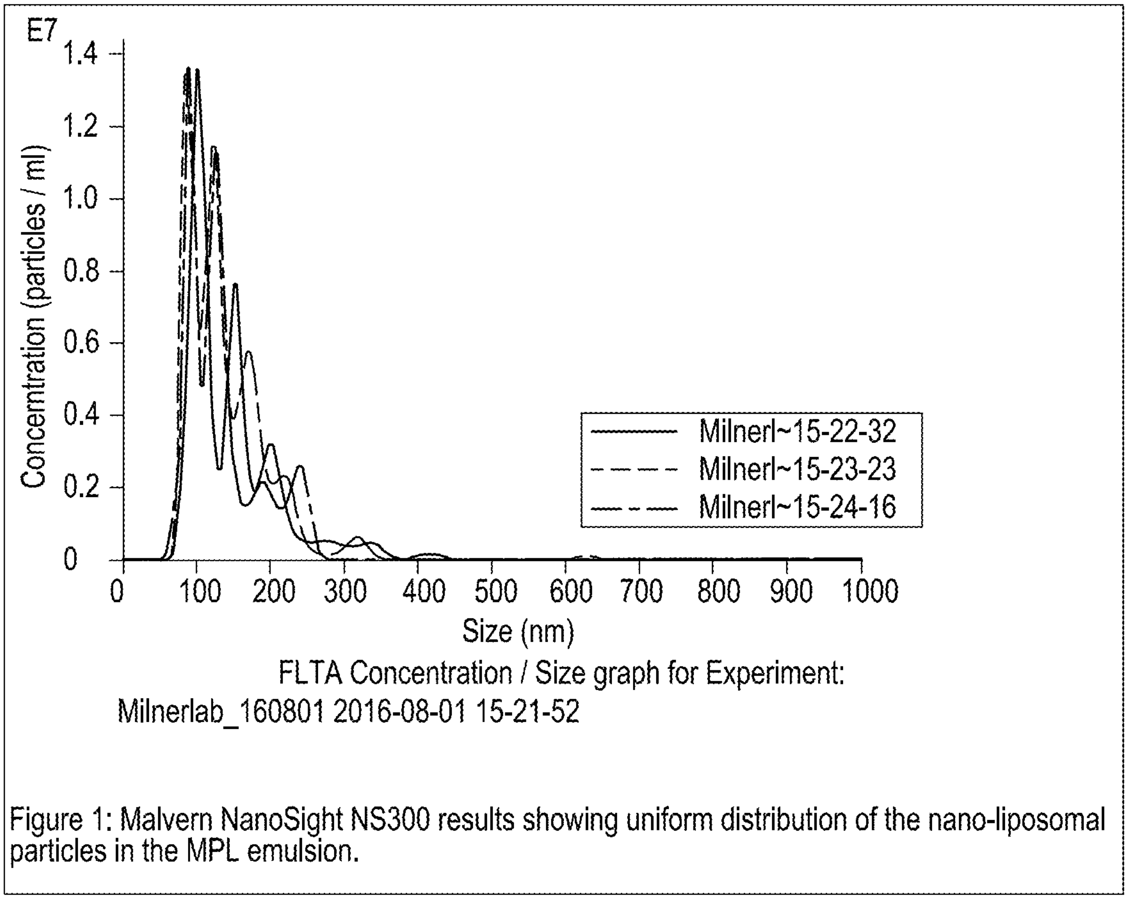
FIG. 1 is a graphical illustration showing distribution of nano-liposomal particle concentration in MPL emulsion.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook, Molecular Cloning: A Laboratory Manual, 2d ed., Cold Spring Harbor Laboratory Press, Cold Spring Harbor, N. Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Kandel, Schwartz, and Jessell, eds., Principles of Neural Science, 4th ed., McGraw-Hill/Appleton & Lange: New York, NY (2000). Unless defined otherwise, all technical and scientific terms used herein have the same meaning as commonly understood by one of ordinary skill in the art.

By way of specific example, the term "primary constituent" refers to molar ratio of MPL relative to phospholipid content in the liposome. In this context, MPL, for example, is a primary constituent if it constitutes a molar ratio relative to total phospholipid (MPL: phospholipid) of 1:10 or greater of the liposome. In a more specific non-limiting example, MPL may constitute a molar ratio of at least 1:4 of the liposome, as its primary constituent. Further still, in another non-limiting embodiment MPL may constitute a molar ratio of at least 1:3 as the primary constituent of the liposome.

Terms such as "a", "an" and "the" are not intended to refer to only a singular entity but include the general class of which a specific example may be used for illustration. The terminology herein is used to describe specific embodiments of the invention, but their usage does not delimit the invention, except as outlined in the claims.

The terms "animal," "patient," or "subject," as used herein, mean any animal (e.g., mammals, (including, but not limited to humans, primates, dogs, cattle, cows, horses, kangaroos, pigs, sheep, goats, cats, rabbits, rodents, and transgenic non-human animals), and the like, which are to be the recipient of a particular treatment. Typically, the terms "animal" "subject" and "patient" are used interchangeably herein in reference to a human subject or a rodent. The preferred animal, patient, or subject is a human.

The term "administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like.

As used herein, the term "effective amount" refers to a quantity of a vaccine composition or an admixture that is sufficient to produce an intended biological effect.

The term "cancer" as used herein is defined as a hyper-proliferation of cells whose unique trait—loss of normal control—results in unregulated growth, lack of differentiation, local tissue invasion, and/or metastasis. Examples include but are not limited to, melanoma, colon cancer, duodenal cancer, prostate cancer, breast cancer, ovarian cancer, ductal cancer, hepatic cancer, pancreatic cancer, liver cancer, sarcoma, renal cancer, endometrial cancer, testicular cancer, stomach cancer, dysplastic oral mucosa, polyposis, thyroid cancer, cervical cancer, head and neck cancer, invasive oral cancer, non-small cell lung carcinoma, small-cell lung cancer, mesothelioma, transitional and squamous cell urinary carcinoma, brain cancer, neuroblastoma, and glioma. In non-limiting embodiments, cancer may refer to a brain tumor, a sarcoma, particularly an osteosarcoma, or a melanoma as discussed herein.

As used herein, the term "vaccine" refers to compositions that affect the course of the disease by causing an effect on cells of the adaptive immune response, namely, B cells and/or T cells. The effect of vaccines can include, for example, induction of cell-mediated immunity or alteration of the response of the T cell to its antigen. Vaccine can be used for therapeutic administration or prophylactic administration. The effect of vaccine compositions can also be measured by testing antibody levels, for example IgM and IgG levels, or other antibodies in the subject. In other examples, the effect of vaccine compositions may include by identifying whether cell-mediated cytotoxicity has occurred. In certain embodiments described herein, the vaccine may cause an effect on the innate immune response, namely, the invariant natural killer cells (INKT cells). GD3 is often described as a self-antigen, and therefore, to be used as an adjuvant-based immunotherapy, it requires an enhanced immune response to overcome the tolerance of the body to the self-antigen. The term GD3 as used herein includes a ganglioside found and expressed at normal levels on the surface of normal nerve cells and melanocytes; however they have been found herein to be expressed at high levels in cancer tissue, including, for example, osteosarcomas, melanomas, and others. GD3 is a ganglioside, anchored to the plasma membrane through its ceramide lipid, with its varied glycans extending into the extracellular place. The term GD3 as used herein refers to GD3 or GD3 protein mimicry.

The term "GD2" as used herein, like GD3, includes a ganglioside found and expressed at normal levels on the surface of normal nerve cells and melanocytes; however they have been found herein to be expressed at high levels in cancer tissue, including, for example, osteosarcomas, melanomas, and other cancers. GD2 can be sourced from nervous tissue, for example, from human brain or bovine brain and can be obtained via Sigma Aldrich (www.sigmaaldrich.com/catalog/product) or from My BioSource.com (www.mybiosource.com/ganglioside/ganglioside-gd2/654273). The term GD2 as used herein refers to GD2 or GD2 protein mimicry.

In one non-limiting embodiment, the GD2 mimetic described herein may include the amino acid sequence of (SEQ ID NO: 1) EDPSHSLGLDAALFM or (SEQ ID NO: 2) RCNPNMEPPRCWAAEGD. In a non-limiting embodiment, the GD3 mimetic described herein may include the amino acid sequence of (SEQ ID NO: 3) RHAYRSMAEWGFLYS.

In some embodiments, vaccine compositions may be provided herein including GD3 or GD2. However, in other embodiments, the vaccine composition may include either GD3 or GD2. "GD3" as referenced herein is also construed to include GD3 mimetics, and "GD2" as referenced herein is also construed to include GD2 mimetics as described in Popa et al. GD3-replica peptides selected from a phage peptide library induce a GD3 ganglioside antibody response. Federation of European Biochemical Societies Letters 580 (2006) 1398-1404. 18 Jan. 2006. Published by Elsevier B. V. doi: 10.1016/j.febslet.2006.01.063.

As used herein, the term "in conjunction" refers to synchronously or near synchronous timing. In conjunction may include within 12-240 hours of administration of chemotherapy treatment, or within 12-240 hours before chemotherapy treatment, or within 12-240 hours after chemotherapy treatment.

The term "cell sample" as used herein as it pertains to the methods described in the claims includes a cancer cell sample.

Embodiments described herein include methods comprising a chemotherapy treatment regimen to be administered to a subject. The chemotherapy treatment regimen involves the administration to the subject of one or more chemotherapeutic agents. The term "chemotherapeutic agent" as used herein may include the various known classes of chemotherapy including but not limited to platinum-based compounds, vinca alkaloids, taxanes, proteasome inhibitors, alkylating agents, antimetabolites, and antitumor antibiotics. In non-limiting embodiments, platinum-based compounds may include Cisplatin, Carboplatin, or Oxaliplatin. In non-limiting embodiments, Vinca alkaloids may include Vincristine, Vindesine, Vinblastine, or Vinorelbine. Taxanes may include, for example, Paclitaxel or Docetaxel. The proteasome inhibits may include Bortezomib, for example.

The term "enhance" as used herein refers to an increase, a stimulation, or an intensification of the quality or amount. In one non-limiting example, administration of a vaccine to a subject may enhance the production of antibodies in the subject. In some non-limiting embodiments, enhancing the production of antibodies may include stimulating the production of antibodies to an antigen presented. In another non-limiting example, enhancing the production of antibodies may include an increase in antibodies sufficient to overcome an immune tolerance or immune suppression of the subject to the relevant antigen.

Overview

As a result of its metastatic potential, malignant melanoma has a poor response to conventional treatment protocols. Melanoma in humans and canines is an aggressive and highly metastatic cancer. The mucosal forms in both humans and dogs share some genetic and histopathologic features, making dogs a valuable spontaneous disease animal model. In both humans and dogs, malignant melanoma is an aggressive cancer with a high metastatic rate, early in the disease course [62, 93]. While human mucosal and non-UV induced cutaneous melanoma have shared histopathologic and genetic features with canine mucosal and cutaneous malignant melanoma, similarities and differences in mutation profiles between canine (oral) and human mucosal melanoma have been found [94]. These differences in mutation profiles could influence tumor behavior and thus response to treatment. Nonetheless, canine mucosal melanoma serves a valuable role as a large animal translational model for the study of immunotherapeutic agents in naturally occurring cancers where immunotherapy targets are known to occur in both species e.g. GD3 [43, 94]. A key factor for the success of immunotherapy is overcoming tumor-induced host immune tolerance and evasion, which has led to increased research into tumor immunology and the suppressive tumor microenvironment [23]. Within this, myeloid-derived suppressor cells (MDSCs) have recently emerged as a key player in blocking immune effector cell function. [86].

Myeloid-derived suppressor cells (MDSCs) are a heterogeneous population of cells of myeloid origin with immunosuppressive capabilities, which are increased in many human cancers and contribute to tumor immune evasion. Originally identified due to their expansion associated with cancer MDSCs have since been shown to be expanded in other pathologic conditions, including inflammation, trauma and sepsis, but are present only in low numbers in healthy animals (Gabrilovich and Nagaraj, 2009; Goulart et al., 2012). MDSCs have a variety of mechanisms through which they can modulate the host immune response, including production of immunosuppressive mediators such as arginase 1 (ARG1), inducible nitric oxide synthase (iNOS), reactive oxygen species (ROS), IL-10, TGF-β and IFN-γ (Gabrilovich et al., 2012; Khaled et al., 2013). Multiple factors have been shown to be involved in MDSC upregulation in cancer (Gabrilovich et al., 2012; Khaled et al., 2013). Particularly, granulocyte-macrophage colony-stimulating factor (GM-CSF) has been found to drive MDSC formation via bone marrow stimulation (Dolcetti et al., 2009; Lechner et al., 2010; Zhao et al., 2016) and monocyte chemoattractant protein (MCP-1, also known as chemokine (C—C motif) ligand 2 or CCL2) has been shown to have direct effects on cells within the tumor microenvironment, including MDSCs, which promotes tumorigenesis and metastasis (Zhang et al., 2010). Additionally, the MCP-1/CCR2 pathway has been found to have a key role in MDSCs migration to the tumor and on tumor growth (Huang et al., 2007).

In mice, MDSCs are defined by a characteristic co-expression of CD11b and GR1 (granulocyte marker), however human leukocytes have no analogous marker to GR1 and to date, no unique markers for MDSCs have been identified (Bronte et al., 2016; Khaled et al., 2013; Mandruzzato et al., 2016). Nonetheless, progress in analysis of morphology and phenotypic expression of cell surface markers has led to the identification of at least two major MDSC subsets, monocytic (M-MDSCs) and polymorphonuclear (PMN-MDSCs) in both humans and mice and the pattern of major subset expansion has been shown to be variable among different human cancer types (Khaled et al., 2013; Marvel and Gabrilovich, 2015).

To improve interpretation and comparison between human laboratories and studies minimum phenotype definitions of CD11b+CD14−CD15+ (or CD66b+) for PMN-MDSCs and CD11b+CD14+HLA-DRlow/-CD15− for M-MDSCs were recently proposed with functional demonstration of immunosuppressive capacity by T-cell suppression assay recommended to confirm MDSC identification (Bronte et al., 2016). MDSCs are significant contributors to the tumor immune evasion and host tumor tolerance, making them, along with cytokine mediators, attractive targets for therapeutic interventions (Gabrilovich and Nagaraj, 2009). However, to date, only a few studies have been published on MDSCs in dogs, which has limited the ability to investigate these cells as a target in this model.

Immunotherapy remains a crucial therapeutic option in the treatment of melanoma in humans and many different modalities have been used in the effort to improve outcomes (Lindsay et al., 2015). Similarly, the immunotherapy strategies used in canine patients with melanoma have been varied, with the majority using active specific immunity, through the administration of vaccines (Alexander et al., 2006; Bergman et al., 2003; Dow et al., 1998; Finocchiaro et al., 2015; Helfand et al., 1999, 1994; Hogge et al., 1999; MacEwen et al., 1999, 1986; von Euler et al., 2008; Watanabe et al., 2010). Previous work has shown the melanoma cell surface disialoganglioside GD3 to be highly expressed in canine melanoma cell lines and that a disialoganglioside GD3-based vaccine was well tolerated and induced appropriate innate and adaptive immune responses in normal dogs [2]. The tumor promoting capabilities of MDSCs and the MCP-1/CCR2 pathway make them attractive targets for therapeutic interventions and mitigating their effects may help improve responses immunotherapy.

In order to investigate these cells as a therapeutic target, further characterization of MDSCs and their role in individual canine cancers has been determined as described herein. The discoveries herein identified and characterized major changes in MDSC subsets using flow cytometry protocol, using commercially available antibodies in matched normal dogs and dogs with cutaneous and digital melanoma. A feasibility study recapitulated the published protocol and established a baseline for future immunotherapeutic interventional studies. In addition, changes in MDSC subsets were compared overtime in response to the administration of the GD3-based vaccine embodiments described herein in the absence of additional cytotoxic cancer therapy. Lastly, the serum expression profiles of the chemokine MCP-1 and cytokines GM-CSF and IL-10, were assessed along with any correlation of their level in response to the administration of the GD3-based vaccine embodiments.

As aforementioned, MDSCs have been identified herein as a valuable target to improve immunotherapy outcomes. Current information regarding MDSCs in canines is minimal, limiting their use as translational model for the study of MDSCs. Herein, characterization of major MDSCs subsets (monocytic and polymorphonuclear) and the cytokines granulocyte-macrophage colony-stimulating factor (GM-CSF), interleukin 10 (IL-10) and monocyte chemoattractant protein-1 (MCP-1) in canines with malignant melanoma has occurred in order to evaluate changes in MDSCs and the cytokines over time in response to a GD3-based active immunotherapy.

Immunotherapy is currently a major field of research in the treatment of cancer, with the goal of using the immune system to prevent tumor development or reject a tumor once development has occurred. The greatest challenge of immunotherapy is that tumors develop in spite of the immune system, which is thought to be, in part, due to an immunosuppressive tumor microenvironment that prevents effective infiltration of immune cells (Tikoo and Haass, 2015; Vesely et al., 2011). Counteracting the immunosuppressive tumor microenvironment is a potential way to hinder mechanisms of tumor evasion and to improve the efficacy of immunotherapy. MDSCs have recently emerged as one of these key players (Tcyganov et al., 2018; Tsai et al., 2014). Embodiments herein use the flow cytometry protocol in whole blood samples from dogs with melanoma to compare changes in MDSC subsets and potential influential cytokines overtime in response to the administration of a GD3-based vaccine embodiment in the absence of additional cytotoxic cancer therapy.

Embodiments described herein include a GD3-antigen vaccine combined with a liposome containing MPL (monophosphoryl lipid A), wherein MPL is a primary constituent of the liposome. The vaccine embodiment provides a cancer vaccine that can be delivered during chemotherapy treatment to stimulate the immune system.

In one embodiment, for example, an intradermal vaccination containing GD3 and adjuvants has been designed. The vaccine embodiment includes CpG oligodeoxynucleotide (CpG-ODN) sequences and an adjuvant to target toll-like receptors (TLR) of the innate immune system. The inclusion of CpG-ODN sequences and an increased GD3 concentration in the vaccine results in an increase in the inflammation response at the injection site.

As described in a study herein, GD3 IgG and IgM antibodies in vaccinated dogs showed increasing titers over time. Cell-mediated cytotoxicity was only detected in peripheral blood mononuclear cells from vaccinated dogs. Combining the tumor antigen GD3 (a known weak self-antigen) with an adjuvant resulted in overcoming tolerance by an innate and adaptive immune response.

The GD3-antigen vaccine is particularly beneficial against melanomas, and in osteosarcomas where surgery and chemotherapy are standard of care treatments. The nano-sized MPL liposome containing GD3 antigen provides increased stabilization, at least in part as a result of a zeta potential of at least negative 17, resulting in a stable nano-liposome.

Lipid and glycolipid mediators are important messengers of the adaptive responses to stress, including apoptosis. In mammalian cells, the intracellular accumulation of ganglioside GD3, an acidic glycosphingolipid, contributes to mitochondrial damage, a crucial event during the apoptotic program. GD3 is a minor ganglioside in most normal tissues. Its expression increases during development and in pathological conditions such as cancer and neurodegenerative disorders, providing a target for use in treatment or prevention of these illnesses.

The vaccine compositions described herein are useful for administration to mammals, particularly humans, to treat and/or prevent and/or control a cancer, particularly a sarcoma or melanoma neoplasm. In some embodiments, the subject may include a mammal, in particular a human, and further, in some non-limiting embodiments a human diagnosed with or at risk for developing a neurodegenerative disorder, a cancer, including a brain tumor, a melanoma or a sarcoma in some examples.

Vaccine compositions containing the gangliosides as described herein may be administered to a patient suffering from a cancer, or a patient at risk of suffering from cancer. In therapeutic applications, gangliosides (GD3) and liposomal MPL and/or nucleic acid compositions are administered to a patient in an amount sufficient to elicit an effective innate and/or adaptive immune response to the cancer antigen, or more particularly, the cancer idiotype, and to at least partially arrest or slow symptoms and/or complications. An amount adequate to accomplish this is defined as "therapeutically effective dose or amount." Amounts effective for this use will depend on, e.g., the particular composition administered, the manner of administration, the stage and severity of the disease being treated, the weight and general state of health of the patient, and the judgment of the prescribing physician.

In at least some embodiments described herein, the gangliosides include ceramide, ceramide and oligosaccharide with one or more sialic acids linked on the sugar chain, MPL and CpGs which are ODNs (unmethylated CpG dinucleotides).

The vaccine composition embodiments of the invention may also be used purely as prophylactic agents. Generally, the dosage for an initial prophylactic immunization generally occurs in a unit dosage range. In one specific, non-limiting example, the dosage may include approximately 300 μl of MPL, 150 μl GD3 (GD3 may include 150 μl of a 1 mg in 1 ml water solution) and 26.8 μl CPG ODN (CpG ODN may be 26.8 μl of 5 mg in a 1 ml water solution) in one dose, or in multiple sub-parts in non-limiting embodiments. Therefore, MPL makes up greater than 60% of the MPL-GD3-CpG ODN combination, in one embodiment, and as such, is a primary constituent of the vaccine composition described herein.

The immunogenicity of the vaccine may be assessed by measuring the specific activity of GD3 specific antibodies (IgG and IgM) obtained from a sample of the patient's blood (Milner 2006). An in vitro cytotoxicity assay was performed using peripheral mononuclear cells (PBMCs) from vaccinated dogs which showed killing of melanoma cells in vitro. In addition, it was shown that the GD3-based vaccine increases natural killer cells (NKT) in a murine C57BL/6 melanoma model when compared to controls (AACR Milner 2018). NKT cells are identified as the effector cells (cancer killing cells) in cancers associated with lipid antigens such as GD3. In addition to immunological end points, the primary tumor size over time, time to metastasis, and overall survival were measured using standard imaging methods known in the art, including, for example, X-ray studies, CT and ultrasound.

The dosage for an initial therapeutic immunization generally occurs in a unit dosage over weeks to months and may be administered depending upon the patient's response and condition as determined by measuring GD3 specific antibodies (IgG and IgM) obtained from a sample of the patient's blood as described above.

The compositions of the present invention may be employed in serious disease states including life-threatening or potentially life-threatening situations. In such cases, as a result of the minimal amounts of extraneous substances and the relative nontoxic nature of the compositions of the invention, it is possible and may be desirable to administer substantial excesses of these compositions relative to these stated dosage amounts.

The compositions for therapeutic treatment are intended for parenteral, topical, oral, intrathecal or local administration. Preferably, the compositions are administered parentally, e.g. intravenously, subcutaneously, intradermally, or intramuscularly. Thus, the invention provides compositions for parenteral administration which comprise a solution of the gangliosides dissolved or suspended in an acceptable carrier, preferably an aqueous carrier. A variety of aqueous carriers may be used, e.g. water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

A human unit dose form of the GD3/MPL composition embodiments described herein is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., *Remington's Pharmaceutical Sciences,* $17^{th}$ Edition, A. Gennaro, Editor, Mack Publishing Co., Easton, Pa., 1985).

The composition embodiments described herein may be administered via liposomes which serve to target the GD3/MPL or other composition embodiments to a particular tissue, such as lymphoid tissue, or to target selectively to infected cells, and/or to increase the half-life of the composition. Liposomes may include emulsions, foams, micelles, insoluble monolayers, liquid crystals, phospholipid dispersions, lamellar layers and the like. In these preparations, the ganglioside to be delivered is incorporated as part of a liposome, alone, or in conjunction with a molecule which binds to a receptor prevalent among cancer cells. Thus, liposomes either filled or decorated with a desired ganglioside as described in embodiments herein, i.e., GD3, and MPL is delivered to an antigen presenting cell (APC), such as a dendritic cell (i.e., Langerhans cell (LC)). The APC thereafter presents the GD3 to the immune system via CD1b, which then activate iNKT cells. These iNKT cells travel to the cancer cell which expresses GD3 and stimulates a cell killing effect on the cancer cell. Liposomes for use in accordance with embodiments described herein invention may be formed from standard vesicle-forming lipids, which generally include neutral and negatively charged phospholipids and a sterol, such as cholesterol. The selection of lipids is generally guided by consideration of liposome size, acid lability and stability of the liposomes in the blood stream. A variety of methods are available for preparing liposomes, as described in, e.g. Szoka, et al., *Ann. Rev. Biophys. Bioeng.* 9:467 (1980), and U.S. Pat. Nos. 4,235,871, 4,501,728, 4,837,028, and 5,019,369. In alternative embodiments, novel methods for forming liposomes according to inventive concepts described herein are provided. In particular, there are described methods for forming novel nano-liposomes for use in the compositions discussed herein for administration to a subject.

For targeting cells of the immune system, a ligand to be incorporated into the liposome can include, e.g., antibodies or fragments thereof specific for cell surface determinants of the desired immune system cells. A liposome suspension containing a composition as described herein may be administered intravenously, locally, topically, or otherwise in a dose which varies according to, inter alia, the manner of administration, the composition being delivered, and the stage of the disease being treated.

For solid compositions, conventional nontoxic solid carriers may be used which include, for example, but are not limited to, pharmaceutical grades of mannitol, lactose, starch, magnesium stearate, sodium saccharin, talcum, cellulose, glucose, sucrose, magnesium carbonate, and the like.

In one embodiment, a vaccine composition for enhancing production of antibodies against disialoganglioside GD3 is provided. The composition may include an admixture of an effective amount of disialoganglioside GD3 to enhance antibody production in a subject; and an effective amount of an adjuvant comprising monophosphoryl lipid A (MPL). In a further embodiment, the composition may include an effective amount of a CpG oligodeoxynucleotide (CpG-ODNs). In yet a further embodiment, the adjuvant targets toll-like receptors (TLRs) in the subject in activation of the adaptive and/or innate immune system.

MPL has an ability to activate antigen presenting cells and induce cytokine cascades. MPL has also been shown to activate monocytes and macrophages (3). By activating these cells, vaccine antigens are more readily phagocytized, processed and presented. MPL also directly stimulates the production of the T helper cell type 1 (Th1) cytokines IL-2 and interferon gamma. In some non-limiting embodiments, the composition may be provided wherein MPL is the primary constituent.

The vaccine composition or admixture embodiments described herein may be administered subcutaneously, intracutaneously, intradermally, intravenously, intraarterially, intratumorally, parenterally, intraperitoneally, intramuscularly, intraocularly, intraosteally, epidurally, intradurally, and the like. Often, the most common routes of vaccination are subcutaneous (SC), intradermal (ID), intravenous (IV), intratumoral (IT) and intraperitoneal (IP). For the embodiments described herein, intradermal injection is the most effective. Local inflammation causes local immunostimulation which later develops into a systemic immune response. This is much less likely to happen at intramuscular or even subcutaneous injection. To the extent that the vaccines are compatible with buffers and/or pharmacologically acceptable salts these can be prepared in aqueous solution suitably mixed with one or more additives. Under ordinary conditions of storage and use, these preparations may include limited amounts of a preservative and/or an antibiotic to prevent the growth of microorganisms.

Moreover, in some embodiments, the composition may include an oil-in-water emulsion. Emulsions may cause tissue damage at the site of injection, resulting in non-specific inflammation, attraction of macrophages, and the inception of the immunological cascade. Antigens associated with oil droplets in the emulsion become more particulate in nature. particulates are more readily trapped in the lymph node and taken up by macrophages and dendritic cells, leading to enhanced antigen presentation. MPL complements and enhances the adjuvant activity of an oil-in-water emulsion due to its amphiphilic nature, by associating with the oil droplets and distributing along the oil and water interface. In a further embodiment, the oil in water emulsion includes liposomes that include the MPL.

The liposomes described herein may include a size of 139.9 SD±57 nm. In some non-limiting embodiments, the liposomes include a zeta potential of negative 20-10 mV, in another embodiment, the zeta potential may be negative 17.32±3.02 mV.

Other embodiments described herein include a method of treating a cancer, for example, a melanoma and/or a sarcoma in a subject, comprising vaccinating a subject by administering to the subject an effective amount of the vaccine composition described herein in embodiments, wherein the vaccine composition is effective to produce antibodies against disialoganglioside GD3. The administration may occur in conjunction with a chemotherapy treatment regimen in the subject. In some examples, administration in conjunction with chemotherapy treatment may include within 24-72 hours of chemotherapy treatment, which may include the 24-72 hours prior to chemotherapy treatment, or 24-72 hours after chemotherapy treatment. In conjunction also includes administration which occurs during chemotherapy treatment.

In one embodiment, the administration may include at least four vaccinations. In another embodiment, the administration may include at least three vaccinations. In yet another embodiment, the administration may include at least two vaccinations. The administration may occur at multiple administration sites on the subject. In some examples, multiple-site administration may be provided to identify local reactions at the administration sites. The administration sites, in one example, may occur at sites with easily accessible draining lymph nodes for fine needle aspirate sampling. In non-limiting examples, the sites may include the left shoulder, right shoulder, and one gluteal administration site.

In another embodiment, a method of producing a GD3-liposome composition is provided. In a particular embodiment, the liposome comprises a nanoliposome. In one embodiment, the method includes obtaining a liposome composition wherein the liposome composition comprises monophosphoryl Lipid A containing liposomes and combining an effective amount of a disialoganglioside GD3 self-antigen and CpG ODN to the liposome composition. The nano-liposomes in the emulsified composition may have a size of 139.9 SD±57 nm, in one embodiment. In another embodiment, the nano-liposome in the composition may include a mean Zeta-potential of −17.32±3.02 mV.

In another embodiment, the method of producing a GD3-liposome composition may further include producing the liposome composition by combining amounts of Lipid A, squalene, lecithin, Tween 80 and water to form a mixture; and sonicating the mixture for a time sufficient to form an emulsion. In yet another embodiment, the method may include storing the liposome composition for at least 24 or 48 hours before combining with GD3 and CpG-ODN.

Materials and Methods

Materials and Methods for Example 1

In embodiments described herein, preparation of the novel nanolipo-GD3 composition includes MPL (Sigma Aldrich, St. Louis, MO (L6895), 5 mg bottle), CPG-ODN (Alpha Diagnostics, San Antonio TX (ODN2007-5)) Type B) and GD3 (Matreya LLC, State College PA, (SPL1504, GD3 NH4+ salt). The MPL formulation is prepared [4] and sonicated. The nanolipo-GD3 immunotherapy is prepared fresh at the time of vaccination, in some embodiments, by combining the constituents (300 μl of MPL, 150 μl GD3 and 26.8 μl CPG ODN 2007). The composition comprising the prepared emulsion (476.8 ul) may be administered intradermally. In some embodiments, the administration may occur at three separate sites (for example, left & right shoulder and left gluteal area). The three separate administration sites provides the ability to follow local reaction at vaccination sites and with easily accessible draining lymph nodes for fine needle aspirate sampling, as needed.

Preparation of Liposomes

Squalene and lecithin combination (SQ+L) is made by adding 600 mg lecithin to 5 ml squalene. 500 uL SQ+L is added to 5 mg of Lipid-A powder (Sigma Aldrich, St. Louis, MO (L6895)) plus (4.5 ml $H_2O$ plus Tween 80 [250 uL]) giving MPL. The mixture is then sonicated and refrigerated [4].

Normal Dog Trial (2006)

In normal dog trials, the vaccine embodiments included a RIBI adjuvant. Dogs showed local reactions from the adjuvant and showed a GD3 specific IgM and IgG response. As a result of these trials, no autoimmunity was seen, and no evidence of depigmentation was found. Further studies were conducted with dogs with melanoma and osteosarcoma and included the MPL adjuvant described in embodiments herein.

Materials and Methods for Example 2

Figure 13:
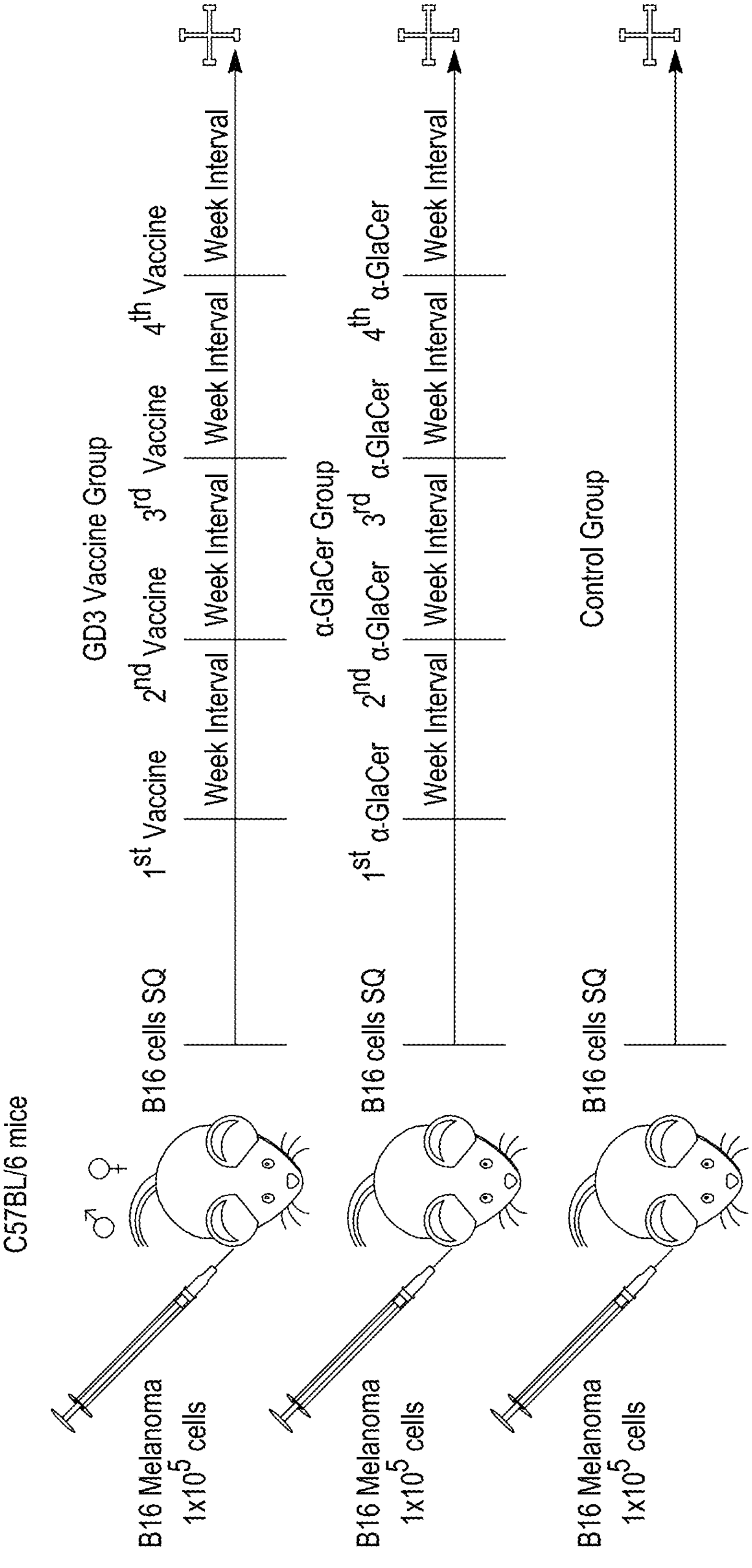
FIG. 13 is a diagram of a study of B16-F10 mouse melanoma cell line in C57/BL6 mice. Three groups of mice were injected with B16 melanoma cell lines. Only one group received the GD3 based vaccine, the other groups were a control group and α-galactosylceramide (α-GalCer), a potent and specific activator of mouse and human iNKT cells.

B16-F10 mouse melanoma cell line in C57/BL6 mice provides a syngeneic model of spontaneous highly metastatic tumor. As shown in the diagram of FIG. 13, three groups of mice were injected with B16 melanoma cell lines. Only one group received the GD3 based vaccine, the other groups were a control group and α-galactosylceramide (α-GalCer), a potent and specific activator of mouse and human iNKT cells. These C57BL/6 mice were vaccinated weekly for 4 weeks followed by a week of rest (see FIG. 13). Mice where then euthanized to collect, blood, liver, and spleen for evaluation of NKT cells. Liver lymphocytes were collected by making mono-cellular suspension of liver obtained after enzymatic digestion. Collected lymphocytes were stained for CD3, CD4, TCRB, NK1.1, CD49b and dead cells. In these experiments untreated and α-galactosylceramide («-GalCer) treated mice were used as controls. Tumor size and mass was only recorded.

Figure 14:
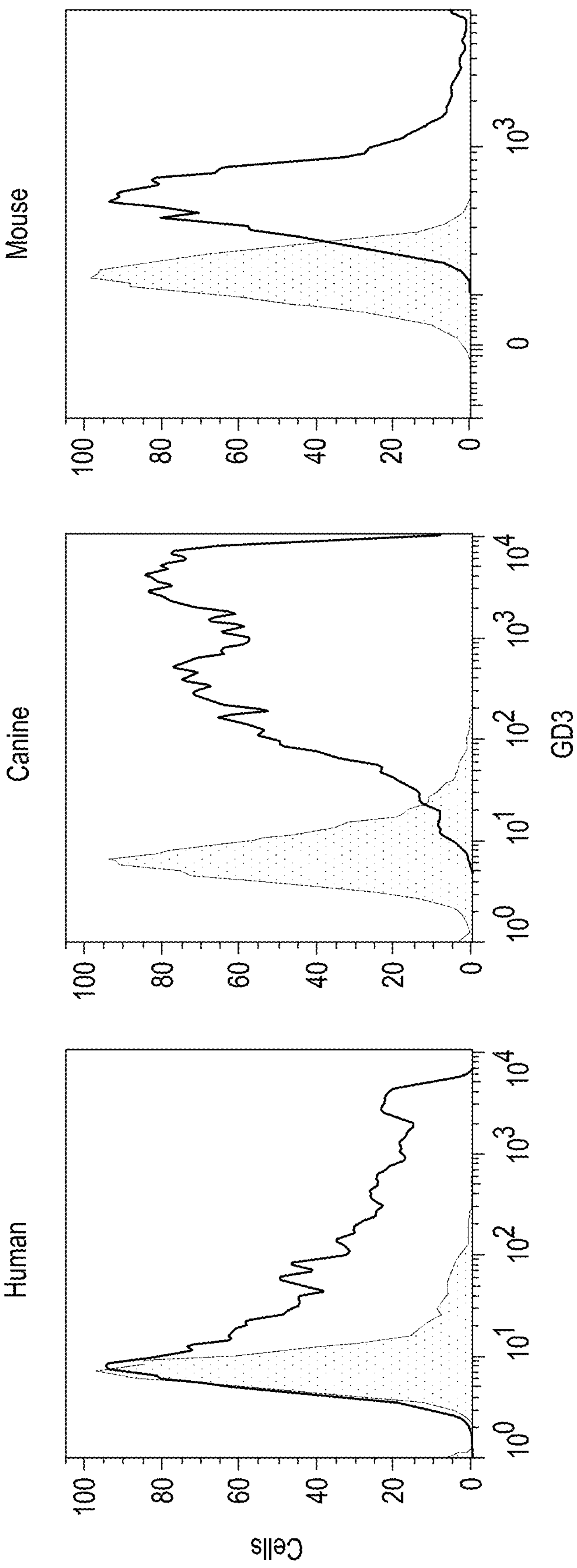
FIG. 14 provides data resulting from A375, CML-2 and B16 melanoma cells which were stained for the presence of GD3. B16 melanoma cells were incubated with an anti-GD3 antibody (Clone R24) (red line) and compared the staining with B16 cells stained with the FITC-tagged anti-mouse secondary antibodies (grey). The stained cells were analyzed with BD Canto and FlowJo 10v.
Figure 15A:
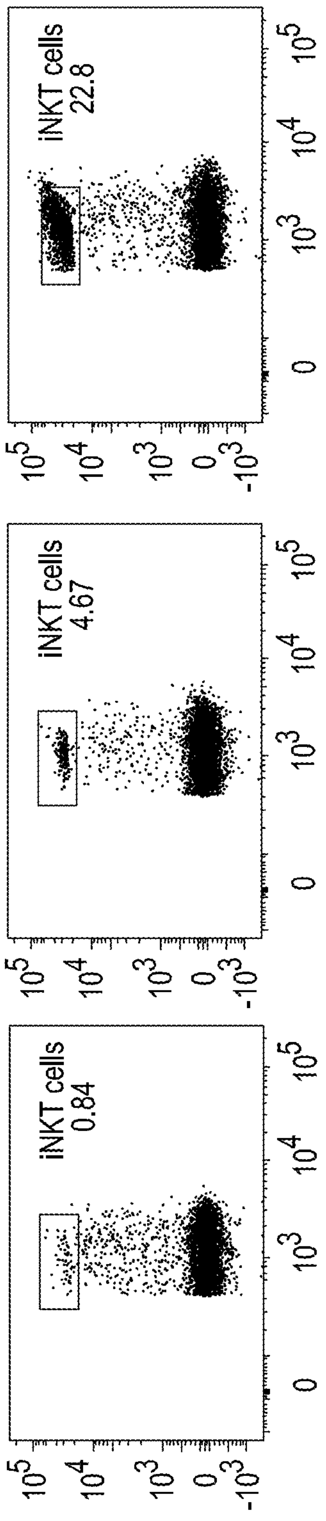
FIGS. 15A-15B demonstrates data of C57BL/6 mice injected with GalCer (IP) or GD3-based vaccine (subcutaneously) four times weekly. One week post last vaccination, mice were euthanized as per IACUC protocol and Natural Killer T cells were evaluated in blood, spleen, and liver by staining the isolated cells with anti-CD45, CD3, CD4, TCRb, CD49b and NK1.1 antibodies. The stained cells were analyzed on BD Fortessa and FlowJo 10v.
Figure 15B:
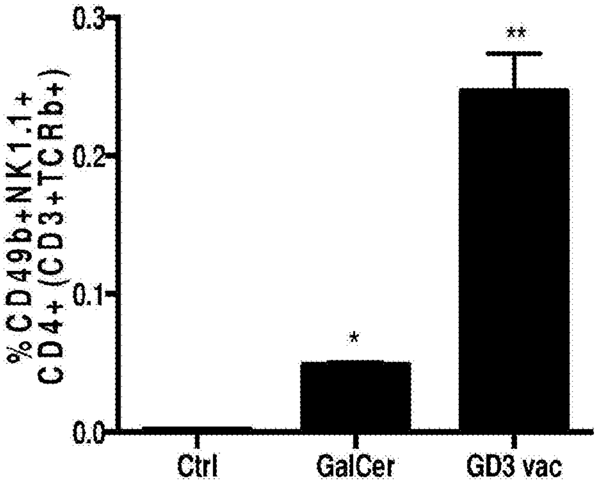

Proof of similar target the expression (GD3) on mouse, human and canine melanoma cell was documented FIG. 14 using flow cytometry. Mice treated with the subcutaneous injections of the GD3 adjuvant vaccine showed an increase in NKT cells (NK1.1+CD49b+CD3+CD4+TCRb+) in the liver but failed to show an increase in the spleen and blood when compared with the untreated mice (See FIG. 15A). The mice treated with α-GalCer also showed an accumulation of NKT cells in the liver; however, the increase in the livers obtained from vaccine-treated mice was 5-10-fold higher compared to the α-GalCer treated mice (see FIG. 15B). A serendipitous finding of statistical differences in tumor weight and size between male and female mice (see FIGS. 16B-C) in the GD3 vaccine group compared to controls was found at necropsy. Interestingly a survival difference between the sexes was also noted to GD3 vaccine in the naturally occurring mucosal melanoma (2), with sterilized females living longer than neutered male dogs (see FIG. 16A).

It has been shown herein that combining GD3 with nano-liposome results in increase in iNKT cell in mice over time. iNKT cells are specific to the immune response to GD3 (see Rowan J. Milner. A protective GD3-based vaccine increases NKT-cells in a C57BL/6 murine model. In: Proceedings of the Fourth CRI-CIMT-EATI-AACR International Cancer Immunotherapy Conference: Translating Science into Survival; Sep. 30-Oct. 3, 2018; New York, NY. Philadelphia (PA): AACR; Cancer Immunol Res 2019; 7 (2 Suppl): Abstract nr A204).

Materials and Methods for Examples 3-4

Vaccine Trials

Melanoma Vaccine Trial: Vaccine Protocol

In phase I, 65 dogs were enrolled and were vaccinated monthly for 3 times (intradermally) at 3 different sites. CBC and serum and staging radiographs and immune monitoring were done. Follow up was done at one-month post vaccinations and then every 6 months until progression. The trial accrued mainly Stage III oral high-grade melanoma (70%).

In phase II 65 dogs were enrolled and vaccinated monthly for 4 times (intradermally) at 4 different sites. CBC and serum and staging radiographs and immune monitoring were done. Follow up was done at one-month post vaccinations and then every 6 months until progression. Similar to the trial accrued mainly Stage III oral high-grade melanoma (70%).

In phase III (open ended), 400 dogs were enrolled and vaccinated monthly for 4 times (intradermally) at 4 different sites followed by 6 monthly boosters. CBC and serum and staging radiographs and immune monitoring were done. Follow up was done one month post initial vaccinations and then every 6 months for a booster until progression. Similar to the trial accrued mainly Stage III oral high-grade melanoma (70%).

Osteosarcoma Vaccine Trial: Vaccine Protocol

Figure 5:
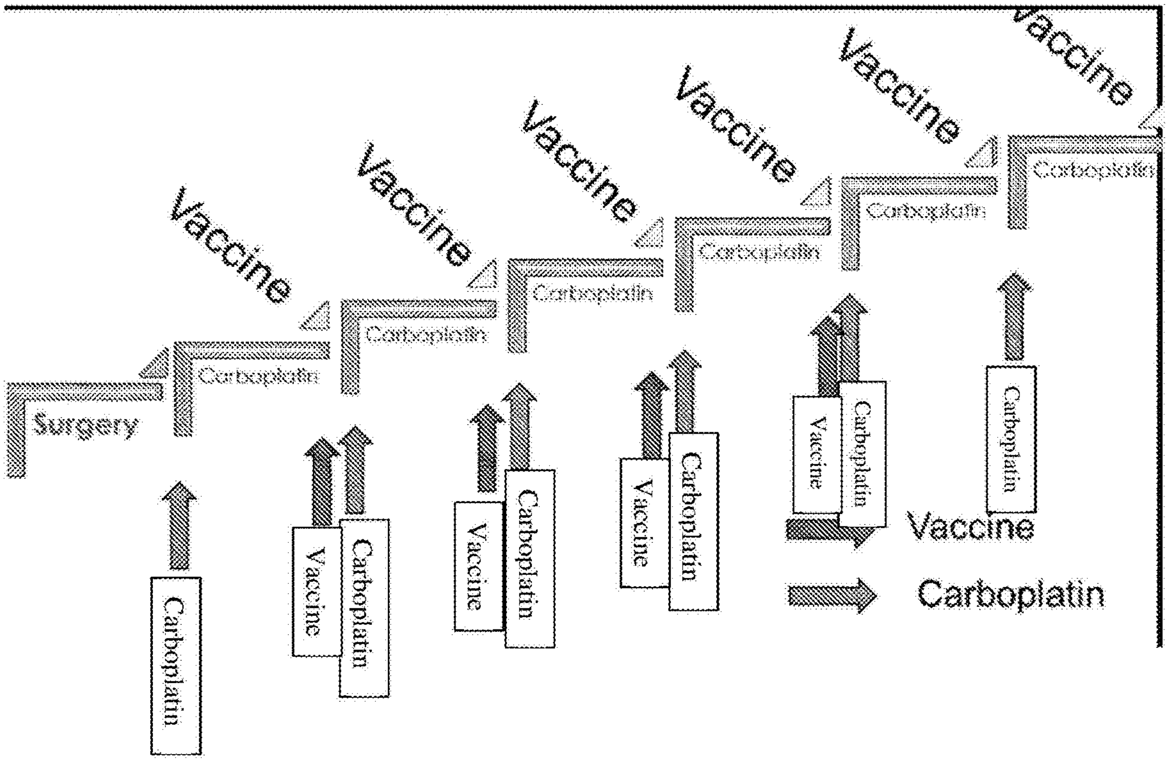
FIG. 5 is a vaccine protocol for an osteosarcoma vaccine trial.

The osteosarcoma vaccine protocol is shown in FIG. 5. The osteosarcoma vaccine trial included two phases. The vaccine group included 25 dogs (n=25). In Phase I, all osteosarcoma dogs underwent amputation followed by a first dose of carboplatin, which was followed by a GD3 vaccination (×4) 2 weeks post carboplatin. The dogs were followed similar to the melanoma cases with regards to staging and other conditions.

In phase II all osteosarcoma dogs underwent amputation followed by the first dose of carboplatin, which was followed by a GD 3 vaccination (×6) 2 weeks post carboplatin. The dogs were followed similar to the melanoma cases with regards to staging and other conditions. Results of the osteosarcoma vaccine trial are shown in FIGS. 6-9.

Materials and Methods for Examples 5-9

Study Populations

Canine patients were prospectively enrolled into two group populations. The first patient group consisted of dogs with a cytologic or histopathologic diagnosis of oral, digital or cutaneous melanoma (melanoma population, abbreviated as MM). Additional inclusion criteria for the melanoma population were staging within two weeks of study entry with chemistry, CBC, urinalysis, three view thoracic radiographs, and regional lymph node aspirates when obtainable, and an expectation of a minimum of 4 months survival time. All patients were staged at study entry according to the World Health Organization (WHO) scheme for dogs with oral melanoma (Table 1) (Owen, 1980). Patients with stage I-IV disease were eligible for melanoma population enrollment.

Additionally, tumors were coded for mitotic index (MI), defined as the number of mitotic figures per 10 high power fields, as either high MI or low MI. Based on previously published information, cutoffs of MI≥4 for oral/mucocutaneous tumors and MI≥3 for cutaneous/digit tumors used to define high MI tumors (Smedley et al., 2011). Exclusion criteria included the use of any immune modifying drug (e.g. prednisolone, nutraceutical e.g. Aloe vera, preexisting endocrine disease e.g. hyperadrenocorticism), the presence of any other preexisting cancer other than melanoma or of any active infection.

The second group consisted of age, weight and sex matched dogs belonging to faculty and staff of the hospital and determined to be clinically healthy based on physical exam, CBC and no reported history of neoplasia (control population). Exclusion criteria included known systemic disease, including but not limited to preexisting endocrine disease or active infection and current or recent (within 1 month) use of any prescribed medications or nutraceuticals, including NSAIDS but excluding preventatives (e.g flea, tick and heartworm prevention).

Vaccine Preparation and Administration

The vaccine was prepared from the commercially available reagents monophosphoryl lipid A from *Salmonella enterica* serotype minnesota Re 595 (MPL) adjuvant (Sigma, MS, USA [Product no. L6895]), oligodeoxynucleotides containing cytosine-phosphate-guanine (CpG) oligodeoxynucleotide sequences (CpG-ODNs) (Alpha Diagnostic International, TX, USA [Catalog number ODN2007] CpG-ODN sequence (SEQ ID NO: 4) 5'-TCG TCG TTG TCG TTT TGT CGT T-3') and GD3 (Matreya LLC, Pleasant Gap, PA, USA [Catalog number 1504]) as previously describe (Milner et al., 2006). Vaccine preparation was performed just prior to administration.

The vaccine was administered intradermally to the melanoma population every 4 weeks for a series of four injections. Three separate vaccination sites were used in rotation as follows: the left shoulder at week 0, right shoulder at week 4, right gluteal region at week 8 and left shoulder at week 12. Separate vaccination sites were chosen to allow for monitoring of any acute cutaneous reaction secondary to the vaccine administration or any subsequent skin complications should they occur.

Sample Collection

Blood was collected at each vaccine time point and at a restage visit 1 month after the 4th vaccine in the melanoma population. For the normal control population blood samples were collected at a single time point. All blood samples were collected by jugular venipuncture and divided into a serum separator tube and heparin tube. Serum was allowed to clot for at least 30 minutes before centrifugation at 1640 g for 8 minutes, then aliquoted into two samples and initially frozen at −20 °C before transfer to −80 °C for long term storage until batched use for cytokine analysis. Heparinized whole blood was used for flow cytometry analysis with all samples processed within 24 hours of collection. Heparinized blood samples were stored at 4 °C until processing if processing was delayed for greater than 1 hour.

Flow Cytometric Analysis

The flow cytometric analysis was based on a published protocol (Goulart et al., 2012) which defined the polymorphonuclear myeloid-derived suppressor cell (PMN-MDSCs) subset as the CD11b+MHCII-CD14− cell population, and the monocytic myeloid-derived suppressor cell (M-MDSCs) subset as the CD11b+MHCII-CD14+ cell population. For the MDSC subset evaluation, whole blood samples were incubated with primary unconjugated mouse anti-dog CD11b antibody (AbD Serotec, clone CA16.3E10) or mouse IgG1 isotype control (AbD Serotec) and then RPE-conjugated Rabbit F(ab') anti-mouse IgG (AbD Serotec) secondary antibody for 30 min per incubation.

All incubations were performed at 4 °C in the dark, unless otherwise stated. Following indirect staining, cells were washed and stained with FITC-conjugated rat anti-dog MHCII (AbD Serotec, clone YKIX334.2) and Alexa fluor 647-conjugated mouse anti-human CD14 antibody (AbD Serotec, clone TÜK4) or isotypes controls (AbD Serotec) for 30 min according to manufacturer's protocol. The anti-CD11b and anti-MHCII clones are marketed as canine targeted by their manufacturer, as well as having shown reactivity in several previous studies (Brodersen et al., 1998; Goulart et al., 2012; Lana et al., 2006; Rao et al., 2011). The anti-CD14 clone has shown canine cross reactivity in several previous studies (Goulart et al., 2012; Jacobsen et al., 1993; Lana et al., 2006). Cells were then washed twice before erythrocytes were lysed with BD Pharmlyse red cell lysis buffer (BD, Franklin Lakes, NJ USA) and incubated at room temperature for 25 minutes in the dark. Antibody-labeled cells were then washed twice, fixed with 4% paraformaldehyde at room temperature for 20 minutes before a final wash was performed to remove excess paraformaldehyde prior to being re-suspended in the FACS buffer for flow cytometry analysis. Unstained and single stained samples were prepared for each patient for negative and compensation controls, respectively.

Samples were analyzed on a Becton Dickinson Canto three-laser flow cytometer (BD, Franklin Lakes, NJ USA) and 100,000 events were collected per sample. Quality control was performed daily at initial startup using manufacturer's setup beads (BD, Franklin Lakes, NJ, USA [Catalog number 642412]). Acquisition gate was set to exclude RBC/dead cells. Compensation was set based on single stained samples and unstained control. Post collection analysis was performed with FlowJo Single Cell analysis software (Tree Star, Ashland, OR, USA). Analysis gates were set based on unstained controls. For flow cytometry gating of populations forward scatter (FSC) versus side scatter (SSC) acquisition gate was first set to exclude dead cells. FSC-Area versus FSC-Height was used to exclude doublets and identify the single cell population. Next, CD11b versus MHCII was used to identify the CD11b+MHCII-population, which was then gated as CD11b versus CD14 to identify the CD11b+MHCII-CD14+ (putative M-MDSC) and CD11b+ MHCII-CD14− (putative PMN-MDSC) populations (Goulart et al., 2012). The numbers of putative PMN-MDSCs and putative M-MDSCs were calculated as percentages of the single cell population.

Cytokine Measurement

Serial serum concentrations of GMCSF, IL-10 and MCP-1 were measured using a customized Milliplex MAP Canine cytokine/chemokine kit (CCYTOMAG-90K, EMD Millipore Corporation, Billerica, MA, USA) according to the manufacturer's instructions, with internal quality control. Overnight incubation at 4□ C and a magnetic plate washer were used. All samples, standards and quality controls were analyzed in duplicate. Plates were read using Bio-Plex® MAGPIX™ multiplex reader and accompanying Bio-Plex Manager Software version 6.1 (Bio-Rad Laboratories, Hercules, CA, USA). Intra-assay and inter-assay coefficients of variation as well as minimum detectable concentrations can be viewed online at http://www.millipore.com.

A single canine melanoma cell line (Remi) was trypsinized from T75 flasks and counted using trypan blue exclusion dye. Live cells (1×106) were spun down at 250× gravity in Falcon #2052 tubes (BD, Franklin Lakes, NJ, USA). The supernatant was removed and partitioned into four aliquots, frozen initially at −20□C and then transferred to −80 °C for long term storage until cytokine kit analysis was performed.

Statistical Analysis

Quantitative differences between the two groups were analyzed using unpaired, two-tailed Student's t test or the non-parametric Wilcoxon rank-sum (Mann-Whitney) test, if data was not normally distributed. Differences between >2 groups were analyzed using ANOVA on ranks. For comparing percent MDSCs at vaccine time points a one-way ANOVA on repeated measures was used. Chi-squared analysis was used for comparison of categorical data. For statistical analysis of cytokines the Mann-Whitney Rank Sum Test was used, the concentration was adjusted to the minimum detectable concentration listed by the manufacturer when sample concentration results produced values 0.0 μg/mL. All analyses were performed with Sigma-Plot software (SigmaPlot for Windows, version 13; Systat Software, Erkrath, Germany) and a p-value<0.05 was considered to be statistically significant.

Patient Characteristics

Thirty-three dogs were enrolled in the melanoma population including 19 neutered males and 14 spayed females with a mean population age of 10.56 years (SD±3.43) and median weight of 27.3 kg (IQR 12.25-35.75). Thirty dogs were enrolled in the control population including 13 neutered males and 17 spayed females with a mean population age of 8.98 years (SD±2.75) and median weight of 20.6 kg (IQR 12.25-29.43). Characteristics of the control (n=30) and melanoma populations are summarized in Table 2. Represented breeds were mixed breed, Labrador retriever, Golden retriever, Beagle, Yorkshire terrier, Miniature Schnauzer and other breeds. There was no statistical significance between the melanoma and control populations with regards to sex, weight, gender or age (p>0.05).

Whole blood and serum collected from 30 healthy controls and 33 patients enrolled in the University of Florida melanoma vaccine trial were analyzed by flow cytometry using a published flow cytometry protocol with canine specific CD11b, MHCII and anti-human CD14 antibodies to assess ostensibly polymorphonuclear-MDSC (CD11b+ MHCII-CD14−) and monocytic-MDSC (CD11b+MHCII-CD14+) subsets. IL-10, MCP-1 and both putative MDSCs subsets were significantly elevated in melanoma dogs versus controls. Both putative MDSCs subsets decreased significantly following GD3-based immunotherapy administration but no significant changes in cytokines were seen over time. To our knowledge, this is the first report documenting increased putative monocytic-MDSCs in canine melanoma. This is consistent with human malignant melanoma data, supporting dogs as a valuable potential model for therapeutic intervention studies.

EXAMPLES

Example 1: Preparation and Preliminary Data and of the Nano-Sized Bilayered Liposomal Immunotherapy (Nanolipo-GD3)

One approach in a normal dog study was to measure the immune response elicited by an adjuvant based GD3 immunotherapy [2]. While GD3 is expressed at higher levels in tumors than normal tissue [3], it is considered a self-antigen and therefore requires immune enhancement to overcome tolerance of the body to self-antigen. As a result, an immunotherapy with an immune enhancement has been provided herein. In the one study a hypothesis that normal dogs would respond to what is considered a weak self-antigen (GD3) was tested. In this embodiment, the adjuvant included CpG oligodeoxynucleotide ((CpG-ODNs) (Coley Pharmaceuticals, 2007 CpG-ODN sequence (SEQ ID NO: 4) 5'-TCG TCG TTG TCG TTT TGT CGT T-3')) sequences and RIBI-adjuvant MPL®+ TDM+CWS Adjuvant System (Sigma, MS, USA [Product No. M 6661RIBI]), both adjuvants known to target toll-like receptors (TLR) of the innate immune system. From a cohort of 10 dogs, 4 were vaccinated intradermally 3 times, at 4 weekly intervals with GD3 plus adjuvant, and 4 received only RIBI-adjuvant, and 2 phosphate buffered saline. Caliper measurements were collected for skin reaction at the vaccination site and sera assayed for IgM and IgG antibodies against GD3 and cell-mediated cytotoxicity against a melanoma cell line.

Results from the study found significant differences (P<0.05) between vaccine site reactions, IgM and IgG levels and cell-mediated cytotoxicity between vaccinated and unvaccinated dogs. The addition of CpG-ODN sequences and GD3 to the vaccine increased the inflammation response at the injection site. From the results of this study, it was identified that by combining the tumor antigen GD3 (a known weak self-antigen) and an adjuvant (targeting TLR), tolerance was overcome by an innate and adaptive immune response in this population of normal dogs. The skin reactions were significant and attributed to the adjuvant. An oil-in-water emulsion of monophosphoryl lipid A (MPL) was substituted for RIBI-adjuvant in some embodiments. It has also been discovered herein that emulsifying the monophosphoryl lipid A (MPL) component of the vaccine by sonication produces a stable nano-sized particle of 139.9 SD±57 nm (see FIG. 1). The stability of these nanoparticles has been confirmed via stability tests.

Figure 2:
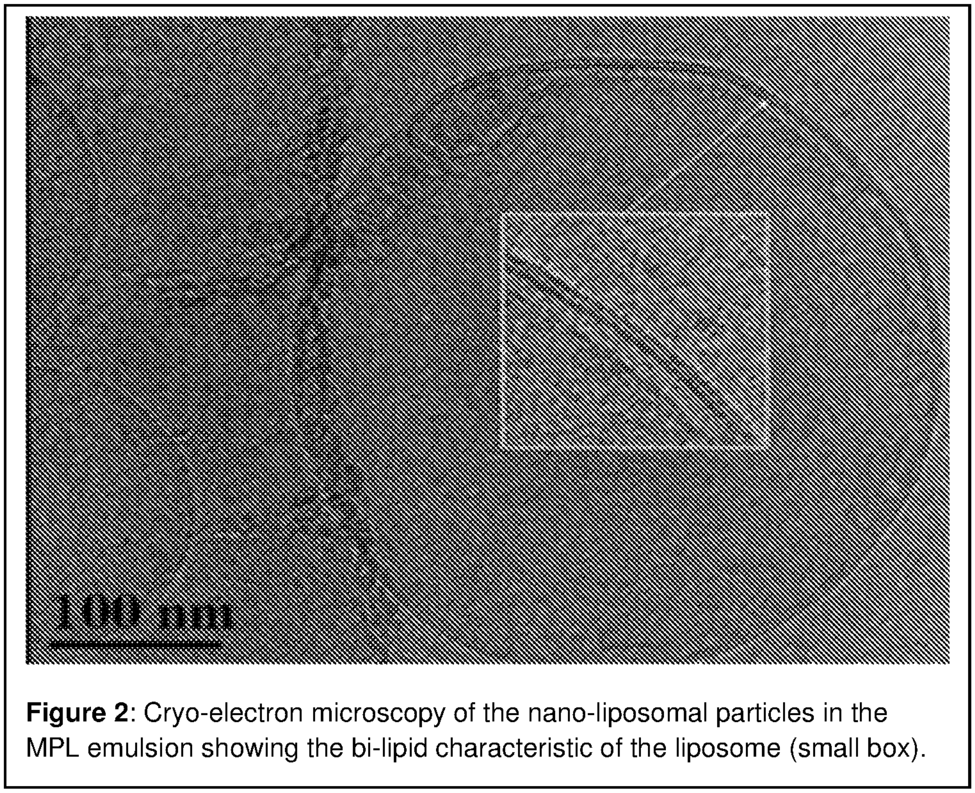
FIG. 2 shows a cryo-electron microscopy slide of nano-liposomal particles.

The nano particle was further explored with cryo electron microscopy which resulted in identification of a bi-lipid layered liposomal (see FIG. 2). Incorporation of MPL as a primary constituent in a liposome is a novel discovery identified herein [4-6]. Enhanced stabilization of the nano-sized liposome in embodiments provided herein is provided by the mean potential negative 17.32±3.02 mV zeta potential, contributing to the uptake of the liposome by antigen presenting cells. As a result of the zeta-potential, providing stabilization in emulsion and protection against aggregation, the liposome embodiments described herein are stable. [6].

Example 2: A Protective GD3-Based Vaccine Increases NKT Cells in a C57BL/6 Murine Model NKT cells are capable of producing different cytokines and chemokines to regulate the overall immune system. After their discovery two decades ago, activation of NKT cells have shown to have a crucial protective role in various infectious, and non-infectious diseases. These cells form a bridge between the innate and adaptive immune cells. The activation and maintenance of these cells are dependent upon the presentation of lipid molecules on CD1 receptors by dendritic cells. Since the target antigen in the vaccine is a lipid (GD3) it is very likely it would be presented on CD1 receptors for the activation of NKT cells. Due to the lack of validated and suitable canine CD1 receptor reagents we were unable to define the mechanism behind the hypothetical protection found in the canine GD3 based vaccine (1). In the murine model NKT cells are well characterized, and provided us with an opportunity to understand the possible selective activation of NKT cells by the GD3 based vaccine. Our data found an increase in NKT cells in the liver for mice vaccinated with GD3 and α-GalCer, but no discernable differences were found in blood and spleen between vaccinated mice and normal controls. Further investigation using the B16 melanoma cell line in C57BL/6 mice vaccinated with the GD3 vaccine and suitable controls may identify the NKT response in the tumor microenvironment.

While the GD3-based vaccine and α-GalCer both increased NKT cells in the murine liver, GD3 increased NKT counts 5-10 fold over α-GalCer. In addition, monitoring changes in NKT numbers in the peripheral blood may not be of benefit due to low cell counts.

See FIG. 14 showing GD3 expression on human, canine and mouse (B16) melanoma cells. A375, CML-2 and B16 melanoma cells were stained for the presence of GD3. B16 melanoma cells were incubated with an anti-GD3 antibody (Clone R24) (red line) and compared the staining with B16 cells stained with the FITC-tagged anti-mouse secondary antibodies (grey). The stained cells were analyzed with BD Canto and FlowJo 10v.

C57BL/6 mice were injected with GalCer (IP) or GD3-based vaccine (subcutaneously) four times weekly. One week post last vaccination, mice were euthanized as per IACUC protocol and Natural Killer T cells were evaluated in blood, spleen, and liver by staining the isolated cells with anti-CD45, CD3, CD4, TCRb, CD49b and NK1.1 antibodies. The stained cells were analyzed on BD Fortessa and FlowJo 10v. (A) A representative dot plot shows an increase in NKT cells in liver but not in blood and spleen (data not shown). (B) A compiled NKT cells data showing a significant increase in the liver of vaccinated mice. n=4, *<P0.05, <P0.01 as shown in FIG. 15**.

Figure 16A:
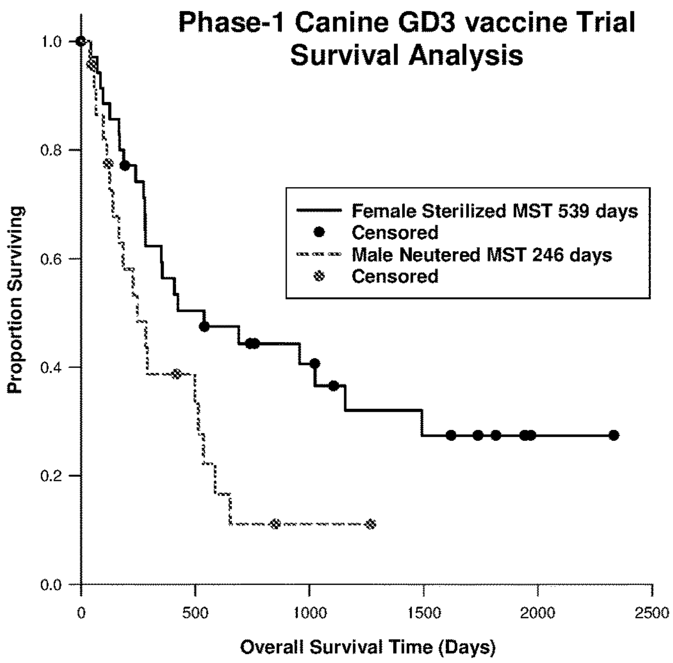
FIGS. 16A-16C provides data resulting from $10^5$ B16 melanoma cells implanted subcutaneously in C57BL/6 male or female mice at left flank with Metrigel. A group of these mice received GD3-based vaccine subcutaneously at the sternum weekly, a day after the tumor implantation, for two weeks (FIG. 16A). Two weeks post-implantation, mice were euthanized and tumor size was measured.
Figure 16B:
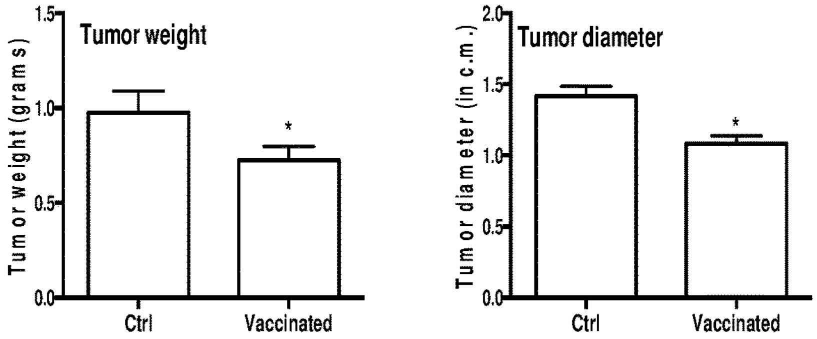
Figure 16C:
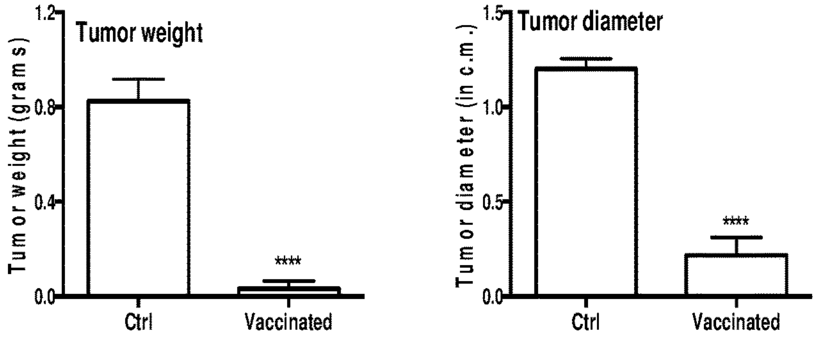

$10^5$ B16 melanoma cells were implanted subcutaneously in C57BL/6 male or female mice at left flank with Metrigel. A group of these mice received GD3-based vaccine subcutaneously at the sternum weekly, a day after the tumor implantation, for two weeks. Two weeks post-implantation, mice were euthanized and tumor size was measured. FIG. 16A shows the tumor size in male mice FIG. 16B shows the tumor size in female mice as a result. n=5, *<P0.05, ****<P0.0001

Example 3: IgG and IgM Specific Immune Response to GD3 Vaccination in Dogs with Melanoma and Normal Dogs FIG. 3 provides the results of the Melanoma Vaccine Trial where verified GD3 IgM and IgG immune response was compared to normal dogs and results are shown in FIG. 3. A transient increase in IgG and IgM was shown. The evidence supports a lack of memory T-cell response, consistent with clinical cases and repeated vaccination. Four vaccines improved survival 2-3 fold over surgery alone (Boston et al., 2014) (see FIG. 4—Kaplan survival curve). Significant elevation of the chemokine CCL2 (MCP-1) was found in vaccinated dogs as compared to normal dogs. No side effects were noted. 1% of subjects may show pain on injection (intradermal).

Figure 4:
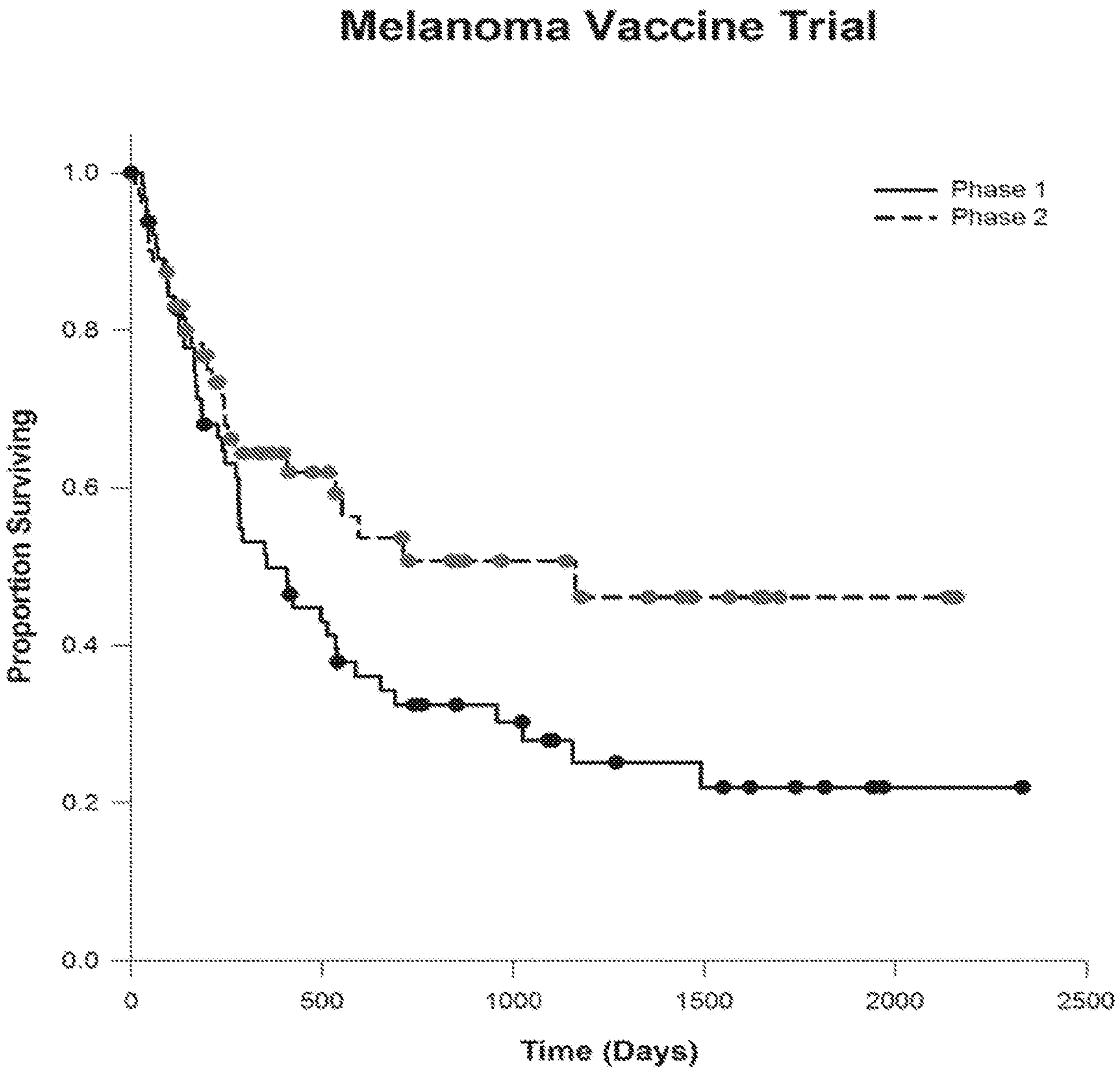
FIG. 4 provides a Kaplan Meyer curve comparing survival times between Phase-1 (median 356 days IQR 1492-166 days) and Phase-2 median (1163 days IQR+inf-210 days (P=0.046) in a melanoma vaccine trial.

The Kaplan Meyer curve of FIG. 4 shows a comparison of survival times between Phase-1 (median 356 days IQR 1492-166 days) and Phase-2 median (1163 days IQR+inf-210 days (P=0.046). Circles represent censored data (IQR—interquartile range) in the Melanoma Vaccine Trial.

Figure 6:
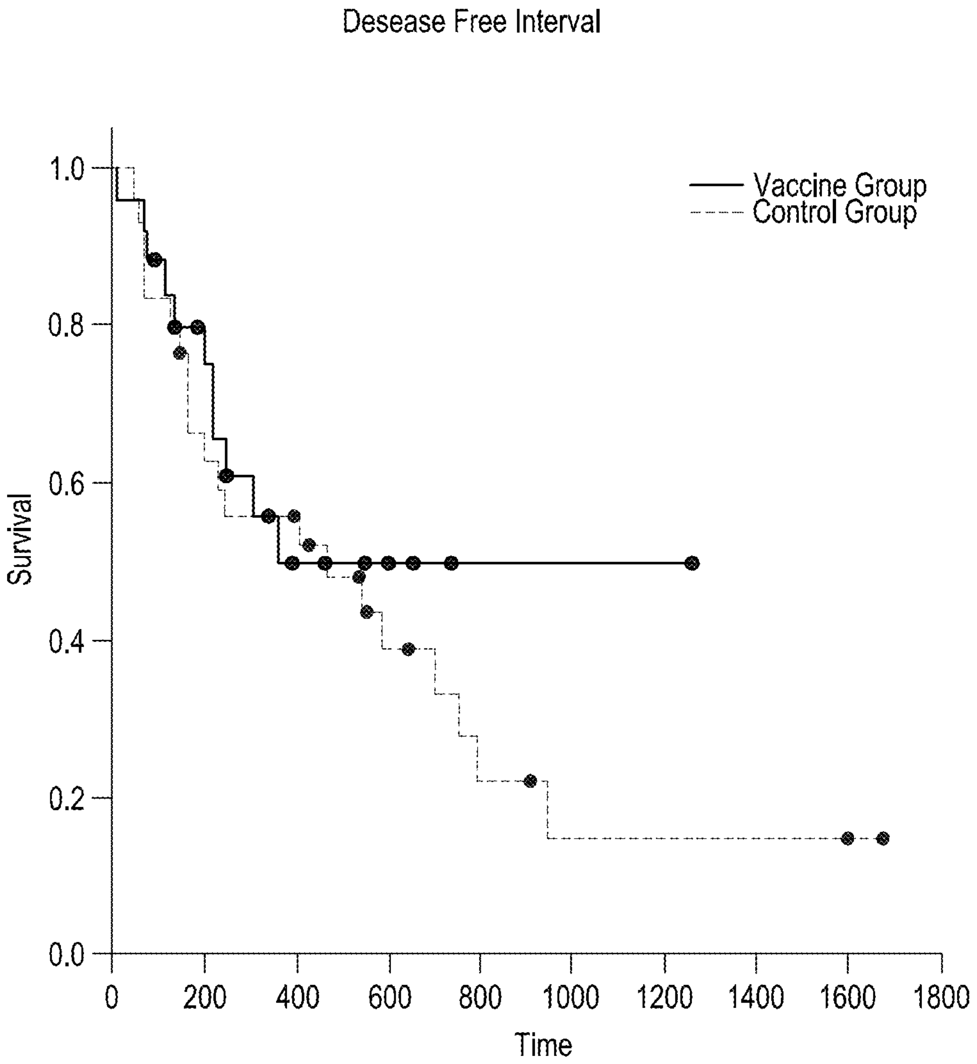
FIG. 6 is a Disease Free Interval (DFI) graphical illustration showing a difference between a vaccine group and a control group of dogs in the osteosarcoma vaccine trial.
Figure 8:
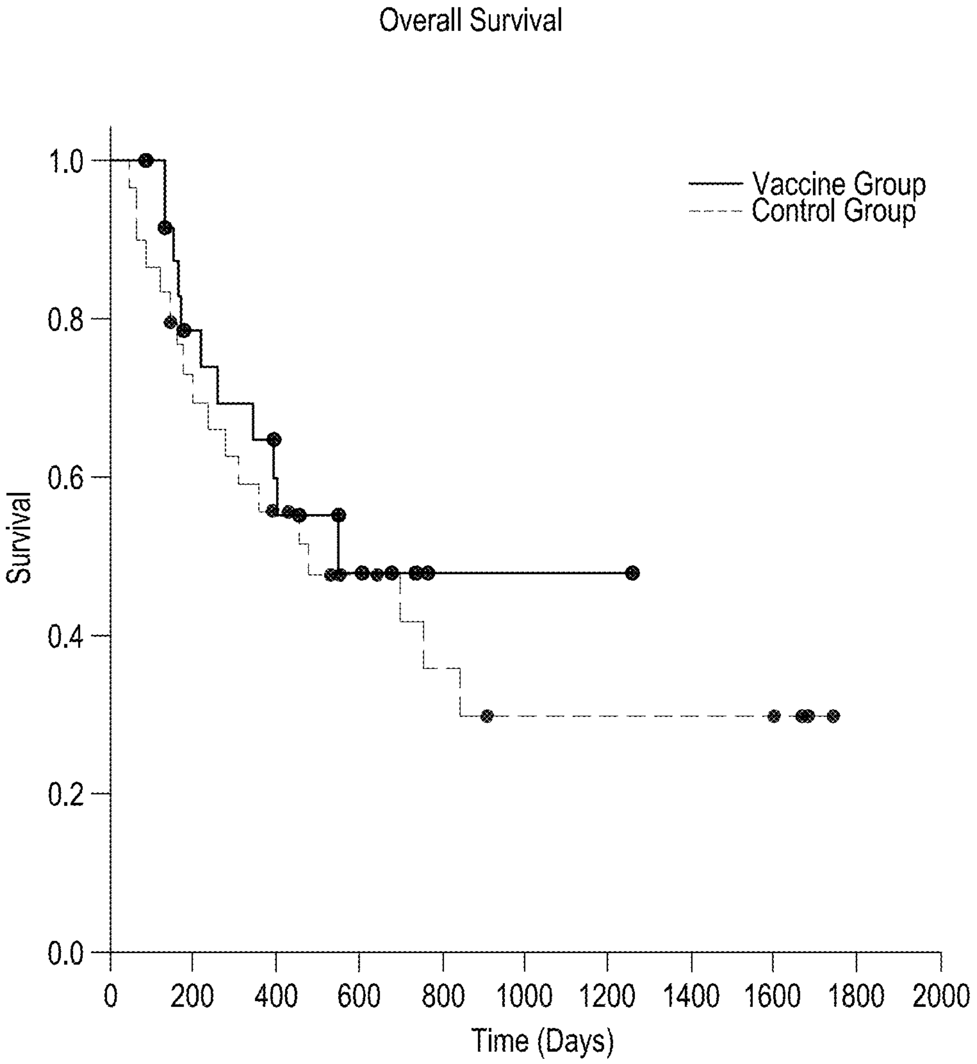
FIG. 8 shows a graphical illustration of the overall survival rates between the vaccine group and the control group after Phase 1 of the osteosarcoma trial.

Example 4: Osteosarcoma Vaccine Trial-Disease Free Survival Rates and Time to Metastasis A schematic of the vaccine protocol for the osteosarcoma vaccine trial is shown in FIG. 5. FIG. 6 provides a graphical illustration of the disease-free interval (time to metastasis) for the osteosarcoma vaccine trial. 5 of the cases were excluded from the results, wherein they received between 1-3 vaccines and failed early on. The survival data for the disease-free interval graph is shown in FIG. 7. In comparison, FIG. 8 provides a graphical illustration of the overall survival rates (n=30 (−5)×30) between the vaccine group and the control group in the osteosarcoma vaccine trial (Phase I). Phase 1 included 25 dogs, who completed 4 vaccines, plus 4-6 rounds of carboplatin. Eight of the twenty-five dogs were still living, ranging 450 days-1258 days (5 cases>551 days). Maintained the median survival of 551 days (75% 221 days 25% not reached) mean 750 days (lower CI 526 days upper CI 975 days). 14 censored—8 still alive, 1 lost to follow up, 5 died of other causes. FIG. 9 provides a table including the overall survival data shown in the graph of FIG. 8.

Both RT-qPCR and RNA FISH studies were performed to identify GD3 synthase and GD2 synthase expression. A level of GD2/GD3 in the cells correlates with the GD2/GD3 synthase which was detected with RT-qPCR and RNA-Scope (RNA FISH), and a correlation was found in the data. GD2 and GD3 were observed in the tissue using RT-qPCR, RNA-Scope and flow cytometry.

Figure 10:
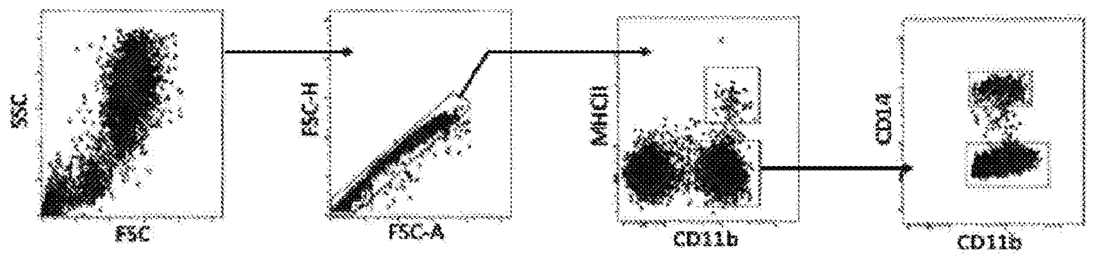
FIG. 10 is a gating strategy for analysis of M-MDSC and PMN-MDSC in canine peripheral blood. Representative flow cytometric analysis of cells from a patient with melanoma. Whole blood was stained with CD11b, MHCII and CD14 antibodies. FSC vs. SSC acquisition gate was set to exclude dead cells. FSC-A vs. FSC-H was used to exclude doublets. CD11b vs. MHCII was used to identify the CD11b+MHCII-population, which was then gated as CD11b vs. CD14 to identify the CD11b+MHCII-CD14+ (M-MDSC) and CD11b+MHCII-CD14-(PMN-MDSC) populations.
Figure 11A:
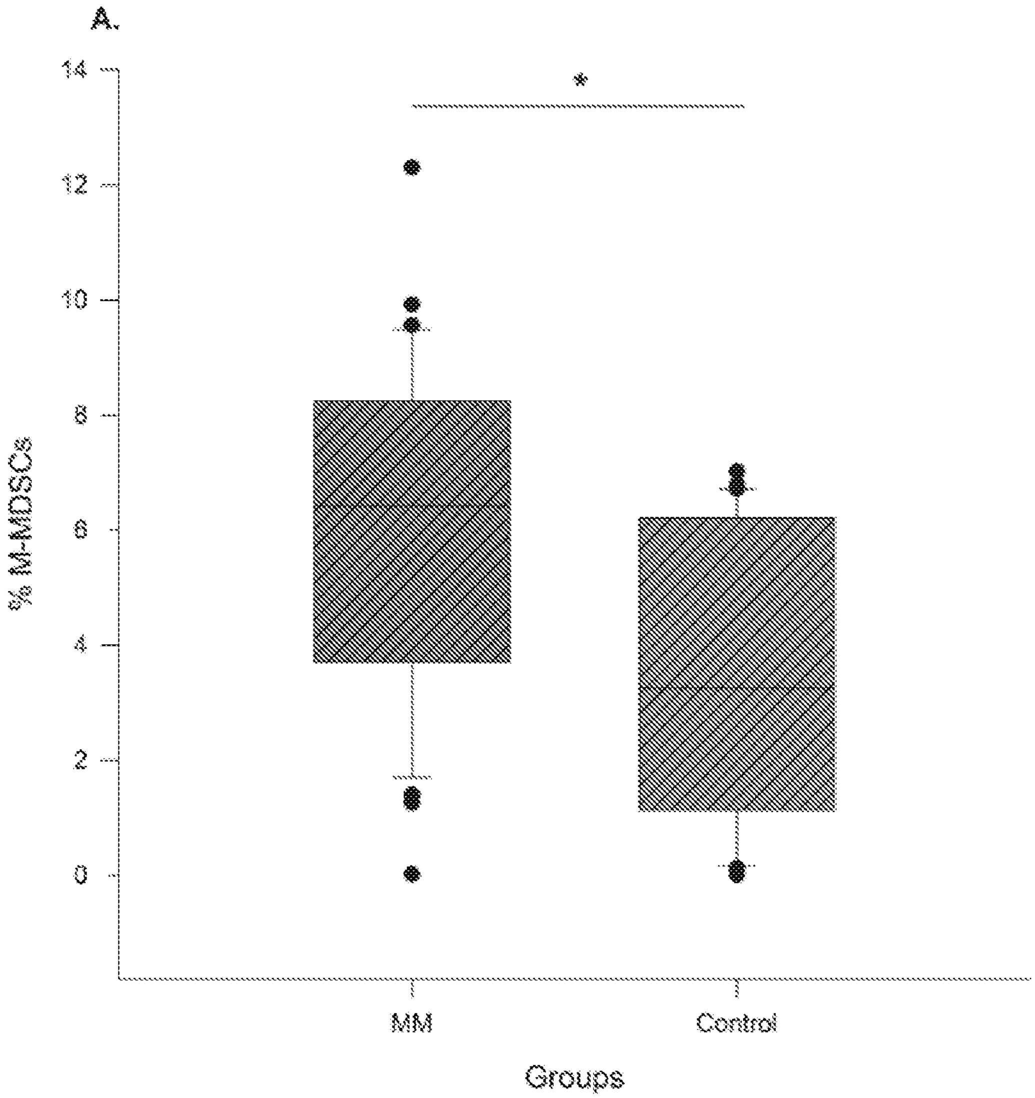
FIGS. 11A-11D provide a comparison of percent M-MDSCs and PMN-MDSCs between melanoma (MM) and control groups and across vaccine time points. Measurements in FIG. 11A and FIG. 11B were at baseline which is equivalent to the vaccine 1 time point in FIG. 11C and FIG. 11D. Box plot, whiskers and dots in FIG. 11A and FIG. 11B represent IQR, 10th and 90th percentile and outliers respectively. Error bars represent standard deviation in the line-scatter plot for FIG. 11C and FIG. 11D. Percent M-MDSCs (FIG. 11A) and PMN-MDSCs (FIG. 11B) were significantly higher in the MM group were compared to the control group (Mann-Whitney Rank Sum Test p=0.001 and p<0.001 respectively). Percent MDSCs decreased from baseline (designated vaccine 1) at each vaccine time point for both PMN-MDSCs (FIG. 11C) and M-MDSCs (FIG. 11D). (ANOVA * p=0.003, ** p<0.001).
Figure 11B:
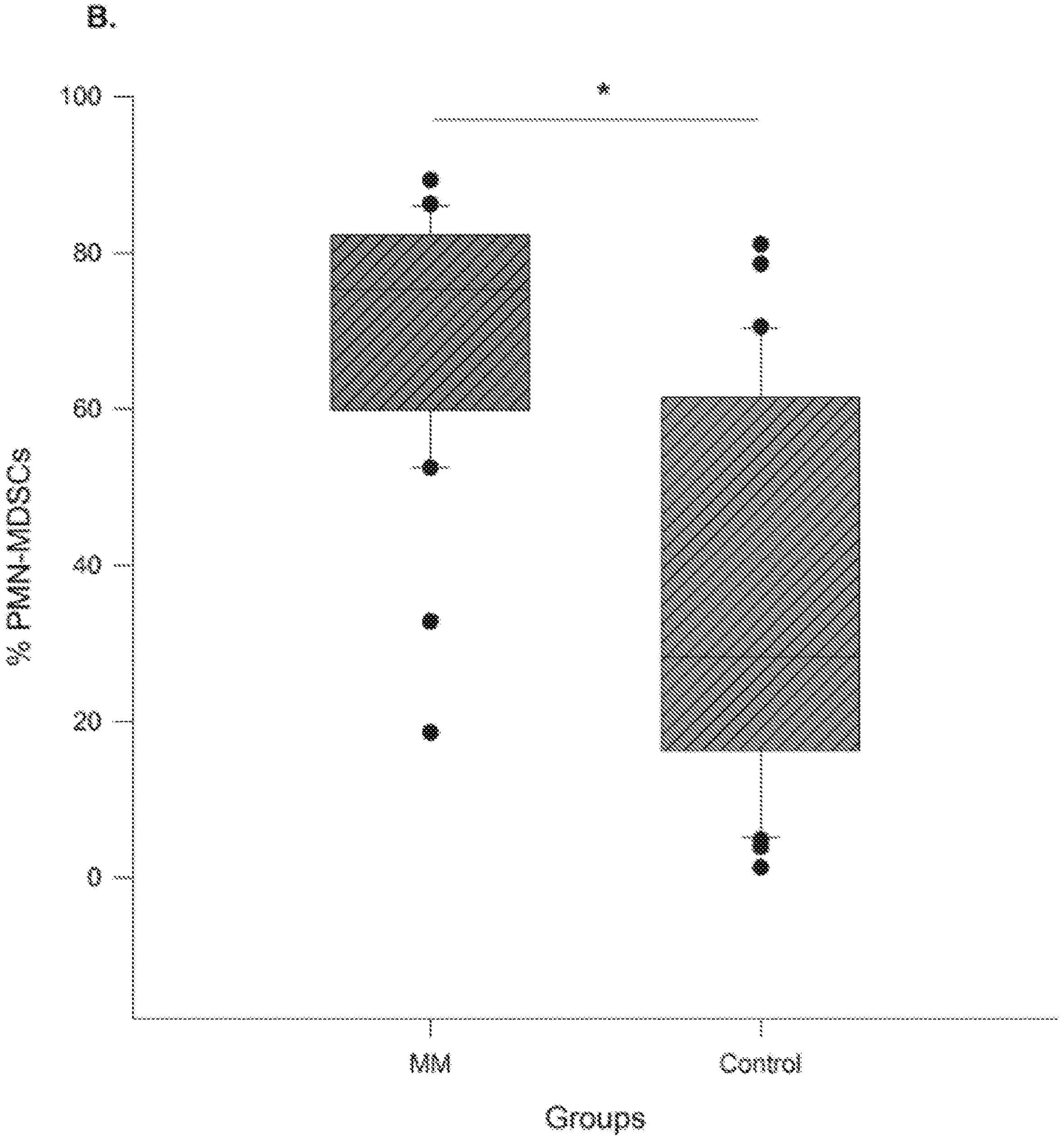

Example 5: Flow Cytometry Characterization of MDSC Subsets in Dogs Showing Baseline The percentages of MDSCs in peripheral blood of melanoma and control populations were evaluated by flow cytometry to characterize the MDSC subsets present in each population as characterized by Goulard et al 2012. Based on commercially available antibodies we defined the polymorphonuclear myeloid-derived suppressor cell (PMN-MDSCs) subset as the CD11b+MHCII-CD14− cell population, and the monocytic myeloid-derived suppressor cell (M-MDSCs) subset as the CD11b+MHCII-CD14+ cell population, using the gating strategy as outlined in FIG. 10. These MDSC subsets in the melanoma population at baseline prior to the first vaccination were compared to the control population. In both the melanoma and control groups, M-MDSCs comprised a relatively small fraction of the overall single cell population but were found to be significantly increased in the melanoma population versus the control population ($p<0.001$) (FIG. 11A). In the melanoma population, the PMN-MDSCs comprised the majority of the single cell population and were significantly increased compared to the control population ($p<0.001$) (FIG. 11B)

Example 6: MDSC Subsets Compared to Stage, Anatomic Location and Mitotic Index

The melanoma population was categorized according to stage, anatomic location and mitotic index (Table 2), which are known prognostic factors for melanoma (Smedley et al., 2011), and then evaluated these in relation to PMN-MDSCs and M-MDSCs populations. Within the melanoma population, there were 15 stage I dogs, 8 stage II dogs, 6 stage III dogs and 4 stage IV dogs. There were no significant differences in MDSC subsets between any stage or between grouped stage I/II versus grouped stage III/IV. Twenty-five of the dogs had oral tumors, 4 had digital tumors and 4 had cutaneous tumors. No significant differences in MDSC subsets of patients with oral/mucocutaneous versus digit versus cutaneous locations were found.

Histopathology was available for 32 patients in the melanoma population for assessment of mitotic index. One patient had a cytologic diagnosis only and was excluded from this portion of the analysis. Tumors were categorized as high-MI if the MI was ≥4 for oral/mucocutaneous tumors or if the MI was ≥3 for cutaneous/digit tumors, tumors below these cutoffs were categorized as low-MI. Twenty-three dogs had high-MI tumors and 9 had low-MI. There was no significant difference in the percentage of PMN-MDSCs and M-MDSCs for high MI tumors versus low MI tumors.

Figure 11C:
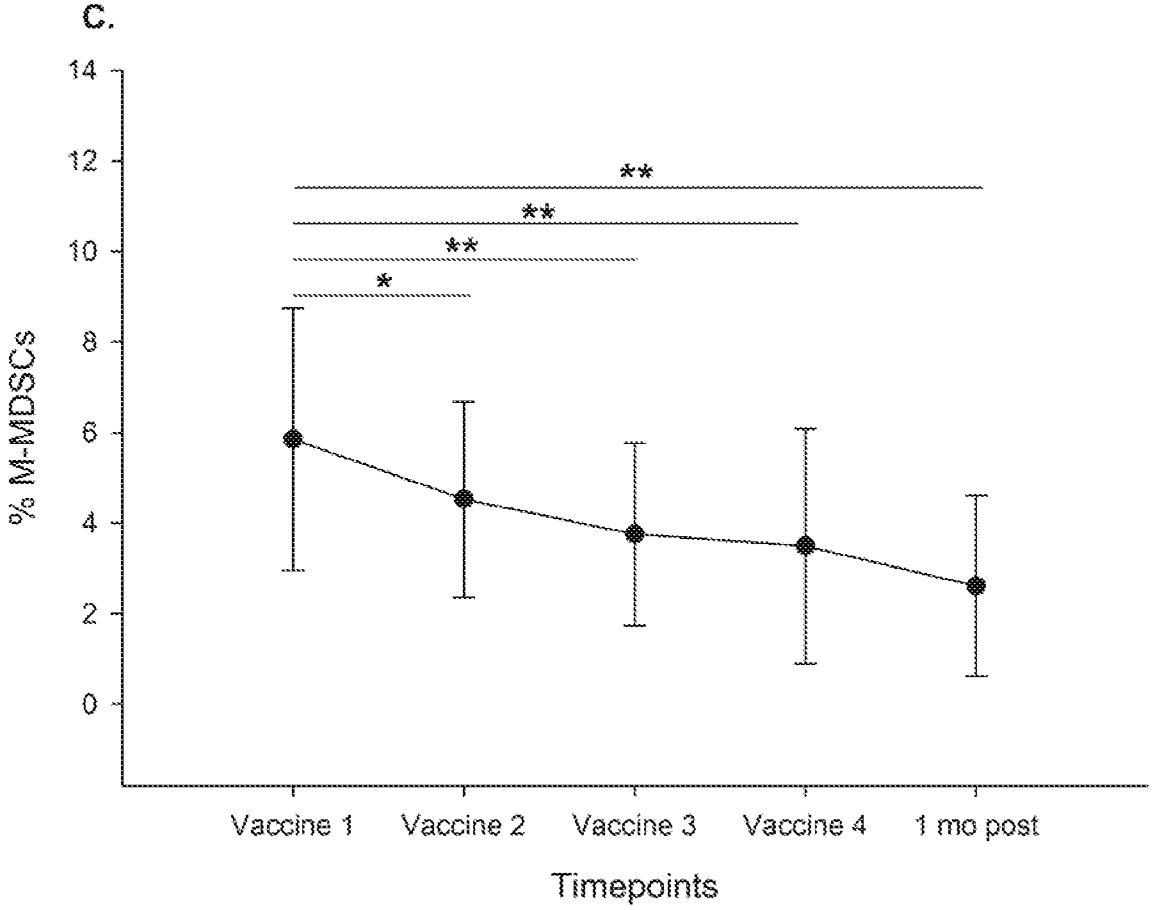
Figure 11D:
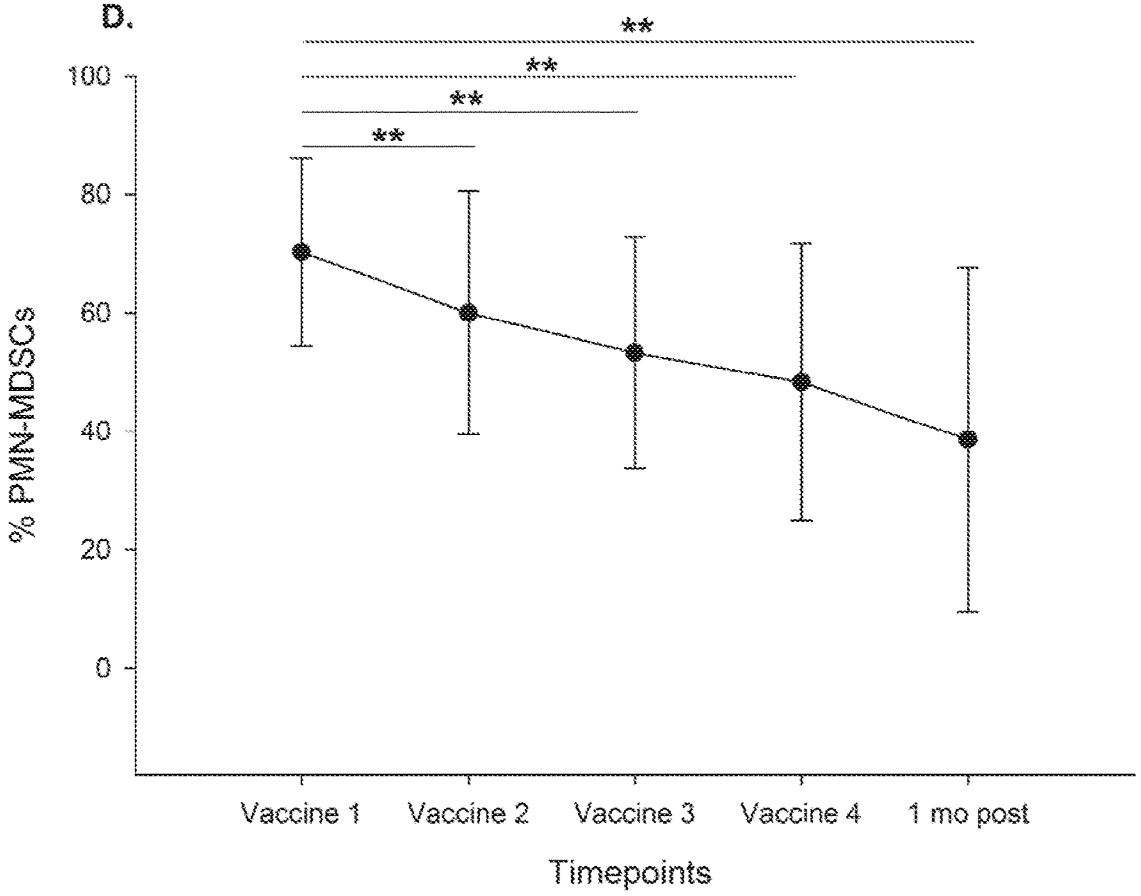

Example 7: MDSC Subset Decreases with GD3-Based Immunotherapy Vaccine Administration In order to determine whether there were any changes in the MDSC subsets in dogs with melanoma over time following four GD3-based vaccine administrations, blood samples were collected prior to vaccination at each of the four vaccine visits and 1 month following the fourth vaccine. The samples were then analyzed using flow cytometry for identification and quantification of the PMN-MDSCs and M-MDSCs. The percentage of both PMN-MDSCs and M-MDSCs decreased significantly each time point, from the second vaccine visit through the 1 month post vaccine visit when compared to the baseline first vaccine visit (($p<0.001$ for all PMN-MDSC time points, $p=0.003$ for M-MDSC second vaccine time point and $p<0.001$ for all other M-MDSC time points), see FIGS. 11C and 11D).

Example 8: Cytokines and Chemokine Profiles in the Melanoma and Control Populations To monitor changes in cytokines and chemokines in dogs with melanoma, serum samples collected prior to vaccination at each of the four vaccine visits and 1 month following the fourth vaccine were analyzed for IL-10, GM-CSF and MCP-1. The median cytokine concentration for the melanoma and control populations at baseline are summarized in Table 3.

Figure 12:
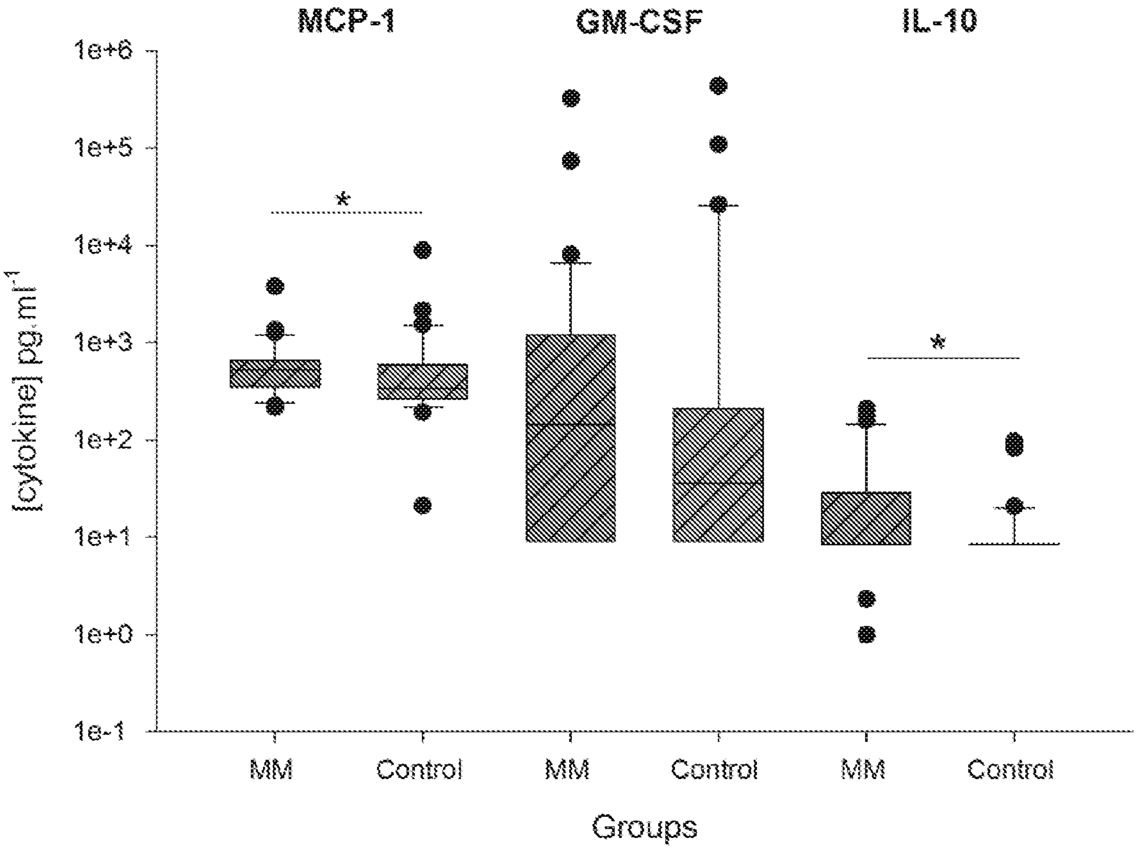
FIG. 12 shows the differences in serum concentrations of MCP-1, GM-CSF and IL-10 between melanoma (MM) and control groups. A log 10 scale was used for the y-axis for best visual display of results. MCP-1 and IL-10 were significantly higher in the MM group compared to control group (Mann-Whitney Rank Sum Test * p=0.035 and p=0.046 respectively). There was no significant difference in GM-CSF concentration between groups (Mann-Whitney Rank. Sum Test p>0.05).

Serum levels of both IL-10 and MCP-1 were significantly higher at baseline in the melanoma population compared to the control population ($p=0.046$ and $p=0.035$ respectively) but not GM-CSF ($p=0.354$) (FIG. 12). Within the melanoma population there were no significant differences in serum levels of GM-CSF, IL-10 and MCP-1 among the five evaluated time points.

A pilot assessment for MCP-1 was performed using a canine metastatic melanoma cell line (Remi) to see if tumor cells were capable of MCP-1 production and to what concentration. The Remi cell line had an MCP-1 concentration of 577.735 μg/mL, which is similar to the median serum MCP-1 concentration of 529.32 μg/mL seen in the melanoma population.

Example 9: Blood Cell Counts at Study Entry in the Melanoma and Control Populations Complete blood cell count (CBC) data was evaluated in both populations to look at the overall cell distribution for identification of possible extreme outliers that might need to be excluded from flow cytometry analysis. No extreme outliers were identified. We were then able to compare the baseline CBC data collected at time of study entry for both groups and prior to vaccination for the melanoma population, for any significant differences between the populations. Median, mean and range for both groups are summarized in Table 4.

The median white blood cell count (WBC), neutrophil and platelet counts were significantly higher in the melanoma population compared to the control population ($p=0.036$, $p=0.002$ and $p=0.025$, respectively). The clinical significance of this finding is unknown as the medians in the melanoma population for WBC ($8.23\times10^3$/ul with IQR 6.405-11.77), neutrophil ($5.99\times10^3$/ul with IQR 4.33-7.519) and platelet counts ($295\times10^3$/ul with IQR 225-391.5) were all within reference ranges. Similarly, for the control population medians for WBC ($7.165\times10^3$/ul with IQR 6.405-11.77), neutrophil ($4.58\times10^3$/ul with IQR 4.33-7.519) and platelet counts ($230.5\times10^3$/ul with IQR 225-391.5) were also within reference range. Five dogs (15%) in the melanoma population had a leukocytosis (ranging from 13.4-$30.4\times10^3$/ul; reference interval 5-$13\times10^3$/ul), characterized by a mature neutrophilia (ranging from 9.24-$26\times10^3$/ul; reference interval 2.7-$8.9\times10^3$/ul). Eight dogs (24%) in the melanoma population has mild to moderate thrombocytosis (ranging from 402-$709\times10^3$/ul; reference interval 134-$396\times10^6$/ul). There were no significant differences in the lymphocyte, monocyte, eosinophil or basophil counts between both group populations.

The mean red blood cell count (RBC) and median hematocrit were significantly lower in the melanoma population when compared to the control population ($p=0.007$ and $p=0.014$, respectively). The mean RBC for the melanoma population ($6.556\times10^6$/ul with SD±0.879) and for the control population ($7.139\times10^6$/ul with SD±0.777) remained within the reference interval. Similarly, the median hematocrit in the melanoma (44.4% with IQR 40.3-49.9) and control populations (48.25% with IQR 43.9-52.675) was also within the reference intervals. Four dogs (12%) in the melanoma population did have RBC counts mildly below reference interval (ranging from 4.69-$5.64\times10^6$/ul; reference interval 5.7-8.3×10$^{6}$/ul) with concurrent mildly decreased hematocrit (ranging from 33.4-39.8%; reference interval 40-56%). All of the anemias were found to be non-regenerative with two being mildly microcytic and normochromic and two being normocytic and normochromic.

TABLES

TABLE 1

Clinical staging system for oral and digital melanomas

| Stage | Tumor size | Regional node status | Distant metastasis |
|---|---|---|---|
| I | <2 cm | Negative | Negative |
| II | 2-4 cm | Negative | Negative |
| III | 2-4 cm | Positive | Negative |
| | >4 cm | Negative | Negative |
| IV | Any | Any | Positive |

Sources: World Health Organization (Owen, 1980), (Manley et al., 2011)

TABLE 2

Patient characteristics for control and melanoma populations

| | Melanoma (n = 33) | Control (n = 30) |
|---|---|---|
| Breed | | |
| Mixed Breed | 14 | 20 |
| Labrador Retriever | 5 | 0 |
| Golden Retriever | 2 | 1 |
| Beagle | 2 | 1 |
| Yorkie | 2 | 0 |
| Miniature Schnauzer | 2 | 0 |
| Other (1 each) | 6 | 8 |
| Age (years) | | |
| Mean (±SD) | 10.56 (±3.425) | 8.98 (±2.75) |
| Sex | | |
| Male, neutered | 19 | 13 |
| Female, spayed | 14 | 17 |
| Weight (kg) | | |
| Median (range) | 27.3 (2.8-48.8) | 20.6 (4.3-40.0) |
| Anatomic Location | | |
| Oral | 25 | |
| Digit | 4 | |
| Cutaneous | 4 | |
| Stage | | |
| I | 15 | |
| II | 8 | |
| III | 6 | |
| IV | 4 | |
| Coded Mitotic Index (n = 32) | | |
| High | 23 | |
| Low | 9 | |

TABLE 3

Summary of GM-CSF, IL-10 and MCP-1 concentrations (pg/mL) at baseline for the melanoma and control populations.

| | Melanoma | | | Control | | | |
|---|---|---|---|---|---|---|---|
| Cytokine | Median | IQR | Range | Median | IQR | Range | p value |
| GM-CSF | 141.36 | 9.2-1194.63 | 9.2-326546.78 | 35.31 | 9.2-209.52 | 9.2-433,897.32 | 0.354 |
| IL-10 | 8.5 | 8.5-28.32 | 0.99-207.96 | 8.5 | 8.5-8.5 | 8.5-96.33 | 0.046 |
| **MCP-1** | **529.32** | **352.35-655.07** | **216.30-3,774.48** | **334.85** | **263.42-599.76** | **21.0-8,886.72** | **0.035** |

Significant differences between cytokine groups are indicated in bold

TABLE 4

Summary of Complete Blood Count (CBC) data and relevant statistics for the melanoma and control populations at baseline.

| | Reference | Melanoma | | | Control | | | |
|---|---|---|---|---|---|---|---|---|
| Parameter | interval | Median | Mean | Range | Median | Mean | Range | p value |
| **WBC** | 5-13 (×10$^3$/μL) | **8.230** | 9.558 | 5.34-30.4 | **7.165** | 7.379 | 2.930-13.42 | **0.036** |
| **Neutrophils** | 2.7-8.9 (×10$^3$/μL) | **5.99** | 6.979 | 2.790-26.0 | **4.58** | 4.676 | 1.8-9.24 | **0.002** |
| Lymphocytes | 0.9-3.4 (×10$^3$/μL) | 1.41 | 1.556 | 0.63-3.46 | 1.73 | 0.606 | 0.38-3.0 | 0.372 |
| Monocytes | 0.1-0.8 (×10$^3$/μL) | 0.45 | 0.565 | 0.0-2.8 | 0.33 | 0.218 | 0.07-0.81 | 0.196 |
| **Platelets** | 134-396 (×10$^3$/μL) | **295** | 330.121 | 174-739 | **230.5** | 257.533 | 136-562 | **0.025** |
| **RBC** | 5.7-8.3 (×10$^6$/μL) | 6.64 | **6.556** | 4.66-8.18 | 7.085 | **7.139** | 5.82-9.07 | **0.007** |
| **HCT** | 40-56% | **44.4** | 44.398 | 32.2-54.7 | **48.846** | 47.513 | 41.6-61.6 | **0.014** |

Data presented as mean, median and range. RBC = red blood cell, WBC = white blood cell, HCT = hematocrit Significantly different between the medians or means of the groups is indicated in bold

REFERENCES

1. Disialoganglioside GD3 on human melanoma serves as a relevant target antigen for monoclonal antibody-mediated tumor cytolysis. Source: Proc. Natl. Acad. Sci. USA Vol. 82, pp. 5155-5159 August 1985 Immunology Author(s): David A. Cheresh, Cyril J. Honsik, Lisa K. Staffileno, Gundram Jung, And Ralph A. REISFELD http://www.pnas.org/content/82/15/5155.full.pdf).
2. Milner R J, Salute M, Crawford C, et al (2006) The immune response to disialoganglioside GD3 vaccination in normal dogs: a melanoma surface antigen vaccine. Vet Immunol Immunopathol 114:273-284. https://doi.org/10.1016/j.vetimm.2006.08.012
3. Dobrenkov K, Ostrovnaya I, Gu J, et al (2016) Oncotargets GD2 and GD3 are highly expressed in sarcomas of children, adolescents, and young adults. Pediatr Blood Cancer 63:1780-1785. https://doi.org/10.1002/pbc.26097
4. Baldridge J R, Crane R T (1999) Monophosphoryl lipid A (MPL) formulations for the next generation of vaccines. Methods San Diego Calif 19:103-107. https://doi.org/10.1006/meth.1999.0834
5. Perrie Y, Crofts F, Devitt A, et al (2016) Designing liposomal adjuvants for the next generation of vaccines. Adv Drug Deliv Rev 99, Part A: 85-96. https://doi.org/10.1016/j.addr.2015.11.005
6. Perrie Y, Kastner E, Khadke S, et al (2017) Manufacturing Methods for Liposome Adjuvants. Methods Mol Biol Clifton NJ 1494:127-144. https://doi.org/10.1007/978-1-4939-6445-1_9
7. Chibowski E, Szcześ A (2016) Zeta potential and surface charge of DPPC and DOPC liposomes in the presence of PLC enzyme. Adsorption 22:755-765. https://doi.org/10.1007/s10450-016-9767-z
8. Anagnostou, V., Smith, K. N., Forde, P. M., Niknafs, N., Bhattacharya, R., White, J., Zhang, T., Adleff, V., Phallen, J., Wali, N., et al. (2016). Evolution of Neoantigen Landscape during Immune Checkpoint Blockade in Non-Small Cell Lung Cancer. Cancer Discov.
9. Baldridge, J. R., and Crane, R. T. (1999). Monophosphoryl lipid A (MPL) formulations for the next generation of vaccines. Methods San Diego Calif 19, 103-107.
10. Boston, S. E., Lu, X., Culp, W. T. N., Montinaro, V., Romanelli, G., Dudley, R. M., Liptak, J. M., Mestrinho, L. A., and Buracco, P. (2014). Efficacy of systemic adjuvant therapies administered to dogs after excision of oral malignant melanomas: 151 cases (2001-2012). J. Am. Vet. Med. Assoc. 245, 401-407.
11. Cheever, M. A., Allison, J. P., Ferris, A. S., Finn, O. J., Hastings, B. M., Hecht, T. T., Mellman, I., Prindiville, S. A., Viner, J. L., Weiner, L. M., et al. (2009). The prioritization of cancer antigens: a national cancer institute pilot project for the acceleration of translational research. Clin. Cancer Res. Off. J. Am. Assoc. Cancer Res. 15, 5323-5337.
12. Chibowski, E., and Szcześ, A. (2016). Zeta potential and surface charge of DPPC and DOPC liposomes in the presence of PLC enzyme. Adsorption 22, 755-765.
13. Dobrenkov, K., Ostrovnaya, I., Gu, J., Cheung, I. Y., and Cheung, N.-K. V. (2016). Oncotargets GD2 and GD3 are highly expressed in sarcomas of children, adolescents, and young adults. Pediatr. Blood Cancer 63, 1780-1785.
14. Lopez, P. H. H., and Schnaar, R. L. (2009). Gangliosides in cell recognition and membrane protein regulation. Curr. Opin. Struct. Biol. 19, 549-557.
15. Milner, R. J., Salute, M., Crawford, C., Abbot, J. R., and Farese, J. (2006). The immune response to disialoganglioside GD3 vaccination in normal dogs: a melanoma surface antigen vaccine. Vet. Immunol. Immunopathol. 114, 273-284.
16. Milner, R. J., Chimura, N., Bowles, K. D., and Salute, M. (2015). Abstract A29: Differential expression of the gangliosides GD3 and GD2 in canine and human osteosarcoma cell lines: An immunotherapy target. Cancer Immunol. Res. 3, A29-A29.
17. Park, J.-E., Wu, D. Y., Prendes, M., Lu, S. X., Ragupathi, G., Schrantz, N., and Chapman, P. B. (2008). Fine specificity of natural killer T cells against GD3 ganglioside and identification of GM3 as an inhibitory natural killer T-cell ligand. Immunology 123, 145-155.
18. Perrie, Y., Crofts, F., Devitt, A., Griffiths, H. R., Kastner, E., and Nadella, V. (2016). Designing liposomal adjuvants for the next generation of vaccines. Adv. Drug Deliv. Rev. 99, Part A, 85-96.
19. Perrie, Y., Kastner, E., Khadke, S., Roces, C. B., and Stone, P. (2017). Manufacturing Methods for Liposome Adjuvants. Methods Mol. Biol. Clifton NJ 1494, 127-144.
20. Skorupski, K. A., Uhl, J. M., Szivek, A., Allstadt Frazier, S. D., Rebhun, R. B., and Rodriguez, C. O. (2016). Carboplatin versus alternating carboplatin and doxorubicin for the adjuvant treatment of canine appendicular osteosarcoma: a randomized, phase III trial. Vet. Comp. Oncol. 14, 81-87.
21. Alexander, A. N., Huelsmeyer, M. K., Mitzey, A., Dubielzig, R. R., Kurzman, I. D., Macewen, E. G., Vail, D. M., 2006. Development of an allogeneic whole-cell tumor vaccine expressing xenogeneic gp100 and its implementation in a phase II clinical trial in canine patients with malignant melanoma. Cancer Immunol. Immunother. CII 55, 433-442. https://doi.org/10.1007/s00262-005-0025-6
22. Athanasiou, L. V., Polizopoulou, Z. S., Papavasileiou, E. G., Mpairamoglou, E. L., Kantere, M. C., Rousou, X. A., 2017. Magnitude of reactive thrombocytosis and associated clinical conditions in dogs. Vet. Rec. 181, 267-267. https://doi.org/10.1136/vr.104042
23. Banerjee, A., Vasanthakumar, A., Grigoriadis, G., 2013. Modulating T regulatory cells in cancer: how close are we? Immunol. Cell Biol. 91, 340-349.
24. Bergman, P. J., McKnight, J., Novosad, A., Charney, S., Farrelly, J., Craft, D., Wulderk, M., Jeffers, Y., Sadelain, M., Hohenhaus, A. E., Segal, N., Gregor, P., Engelhorn, M., Riviere, I., Houghton, A. N., Wolchok, J. D., 2003. Long-Term Survival of Dogs with Advanced Malignant Melanoma after DNA Vaccination with Xenogeneic Human Tyrosinase: A Phase I Trial. Clin. Cancer Res. 9, 1284-1290.
25. Brodersen, R., Bijlsma, F., Gori, K., Jensen, K . . . , Chen, W., Dominguez, J., Haverson, K., Moore, P . . . , Saalmüller, A., Sachs, D., Slierendrecht, W . . . , Stokes, C., Vainio, O., Zuckermann, F., Aasted, B., 1998. Analysis of the immunological cross reactivities of 213 well characterized monoclonal antibodies with specificities against various leucocyte surface antigens of human and 11 animal species. Vet. Immunol. Immunopathol. 64, 1-13. https://doi.org/10.1016/S0165-2427 (98) 00117-2

26. Bronte, V., Brandau, S., Chen, S.-H., Colombo, M. P., Frey, A. B., Greten, T. F., Mandruzzato, S., Murray, P. J., Ochoa, A., Ostrand-Rosenberg, S., Rodriguez, P. C., Sica, A., Umansky, V., Vonderheide, R. H., Gabrilovich, D. I., 2016. Recommendations for myeloid-derived suppressor cell nomenclature and characterization standards. Nat. Commun. 7, 12150. https://doi.org/10.1038/ncomms12150
27. Brusa, D., Simone, M., Gontero, P., Spadi, R., Racca, P., Micari, J., Degiuli, M., Carletto, S., Tizzani, A., Matera, L., 2013. Circulating immunosuppressive cells of prostate cancer patients before and after radical prostatectomy: Profile comparison. Int. J. Urol. 20, 971-978. https://doi.org/10.1111/iju.12086
28. Calvalido, J., Wood, G. A., Mutsaers, A. J., Wood, D., Sears, W., Woods, J. P., 2016. Comparison of serum cytokine levels between dogs with multicentric lymphoma and healthy dogs. Vet. Immunol. Immunopathol. 182, 106-114. https://doi.org/10.1016/j.vetimm.2016.10.009
29. Chang, A. L., Miska, J., Wainwright, D. A., Dey, M., Rivetta, C. V., Yu, D., Kanojia, D., Pituch, K. C., Qiao, J., Pytel, P., Han, Y., Wu, M., Zhang, L., Horbinski, C. M., Ahmed, A. U., Lesniak, M. S., 2016. CCL2 Produced by the Glioma Microenvironment Is Essential for the Recruitment of Regulatory T Cells and Myeloid-Derived Suppressor Cells. Cancer Res. 76, 5671-5682. https://doi.org/10.1158/0008-5472.CAN-16-0144
30. Chun, E., Lavoie, S., Michaud, M., Gallini, C. A., Kim, J., Soucy, G., Odze, R., Glickman, J. N., Garrett, W. S., 2015. CCL2 Promotes Colorectal Carcinogenesis by Enhancing Polymorphonuclear Myeloid-Derived Suppressor Cell Population and Function. Cell Rep. 12, 244-257. https://doi.org/10.1016/j.celrep.2015.06.024
31. Conti, I., Rollins, B. J., 2004. CCL2 (monocyte chemoattractant protein-1) and cancer. Semin. Cancer Biol. 14, 149-154. https://doi.org/10.1016/j.semcancer.2003.10.009
32. Damuzzo, V., Pinton, L., Desantis, G., Solito, S., Marigo, I., Bronte, V., Mandruzzato, S., 2015. Complexity and challenges in defining myeloid-derived suppressor cells: Defining Myeloid-Derived Suppressor Cells. Cytometry B Clin. Cytom. 88, 77-91. https://doi.org/10.1002/cyto.b.21206
33. de Andrés, P. J., Illera, J. C., Cáceres, S., Díez, L., Pérez-Alenza, M. D., Peña, L., 2013. Increased levels of interleukins 8 and 10 as findings of canine inflammatory mammary cancer. Vet. Immunol. Immunopathol. 152, 245-251. https://doi.org/10.1016/j.vetimm.2012.12.010
34. De Sanctis, F., Solito, S., Ugel, S., Molon, B., Bronte, V., Marigo, I., 2016. MDSCs in cancer: Conceiving new prognostic and therapeutic targets. Biochim. Biophys. Acta BBA-Rev. Cancer, The role of the immune system in cancer: from mechanisms to clinical applications 1865, 35-48. https://doi.org/10.1016/j.bbcan.2015.08.001
35. Dolcetti, L., Peranzoni, E., Ugel, S., Marigo, I., Fernandez Gomez, A., Mesa, C., Geilich, M., Winkels, G., Traggiai, E., Casati, A., Grassi, F., Bronte, V., 2009. Hierarchy of immunosuppressive strength among myeloid-derived suppressor cell subsets is determined by GM-CSF. Eur. J. Immunol. 40, 22-35. https://doi.org/10.1002/eji.200939903
36. Dow, S. W., Elmslie, R. E., Willson, A. P., Roche, L., Gorman, C., Potter, T. A., 1998. In vivo tumor transfection with superantigen plus cytokine genes induces tumor regression and prolongs survival in dogs with malignant melanoma. J. Clin. Invest. 101, 2406-2414. https://doi.org/10.1172/JCI510
37. Draxler, D. F., Madondo, M. T., Hanafi, G., Plebanski, M., Medcalf, R. L., 2017. A flowcytometric analysis to efficiently quantify multiple innate immune cells and T Cell subsets in human blood. Cytom. Part J. Int. Soc. Anal. Cytol. 91, 336-350. https://doi.org/10.1002/cyto.a.23080
38. Duffy, A., Zhao, F., Haile, L., Gamrekelashvili, J., Fioravanti, S., Ma, C., Kapanadze, T., Compton, K., Figg, W. D., Greten, T. F., 2013. Comparative analysis of monocytic and granulocytic myeloid-derived suppressor cell subsets in patients with gastrointestinal malignancies. Cancer Immunol. Immunother. 62, 299-307. https://doi.org/10.1007/s00262-012-1332-3
39. Finocchiaro, L. M. E., Fondello, C., Gil-Cardeza, M. L., Rossi, Ú.A., Villaverde, M. S., Riveros, M. D., Glikin, G. C., 2015. Cytokine-Enhanced Vaccine and Interferon-β plus Suicide Gene Therapy as Surgery Adjuvant Treatments for Spontaneous Canine Melanoma. Hum. Gene Ther. 26, 367-376. https://doi.org/10.1089/hum.2014.130
40. Flörcken, A., Takvorian, A., Singh, A., Gerhardt, A., Ostendorf, B. N., Dörken, B., Pezzutto, A., Westermann, J., 2015. Myeloid-derived suppressor cells in human peripheral blood: Optimized quantification in healthy donors and patients with metastatic renal cell carcinoma. Immunol. Lett. 168, 260-267. https://doi.org/10.1016/j.imlet.2015.10.001
41. Gabrilovich, D. I., Nagaraj, S., 2009. Myeloid-derived suppressor cells as regulators of the immune system. Nat. Rev. Immunol. 9, 162-174. https://doi.org/10.1038/nri2506
42. Gabrilovich, D. I., Ostrand-Rosenberg, S., Bronte, V., 2012. Coordinated regulation of myeloid cells by tumours. Nat. Rev. Immunol. 12, 253-268. https://doi.org/10.1038/nri3175
43. Gillard, M., Cadieu, E., De Brito, C., Abadie, J., Vergier, B., Devauchelle, P., Degorce, F., Dréano, S., Primot, A., Dorso, L., Lagadic, M., Galibert, F., Hédan, B., Galibert, M.-D., André, C., 2014. Naturally occurring melanomas in dogs as models for non-UV pathways of human melanomas. Pigment Cell Melanoma Res. 27, 90-102. https://doi.org/10.1111/pcmr.12170
44. Goulart, M. R., Pluhar, G. E., Ohlfest, J. R., 2012. Identification of Myeloid Derived Suppressor Cells in Dogs with Naturally Occurring Cancer. PLOS ONE 7, e33274. https://doi.org/10.1371/journal.pone.0033274
45. Goulart, M. R., Hlavaty, S. I., Chang, Y.-M., Polton, G., Stell, A., Perry, J., Wu, Y., Sharma, E., Broxholme, J., Lee, A. C., Szladovits, B., Turmaine, M., Gribben, J., Xia, D., Garden, O. A., 2019. Phenotypic and transcriptomic characterization of canine myeloid-derived suppressor cells. Sci. Rep. 9, 3574. https://doi.org/10.1038/s41598-019-40285-3
46. Helfand, S. C., Dickerson, E. B., Munson, K. L., Padilla, M. L., 1999. GD3 ganglioside antibody augments tumoricidal capacity of canine blood mononuclear cells by induction of interleukin 12. Cancer Res. 59, 3119-3127.
47. Helfand, S. C., Soergel, S. A., Modiano, J. F., Hank, J. A., Sondel, P. M., 1994. Induction of lymphokine-activated killer (LAK) activity in canine lymphocytes with low dose human recombinant interleukin-2 in vitro. Cancer Biother. 9, 237-244.

48. Hernandez, B., Adissu, H. A., Wei, B.-R., Michael, H. T., Merlino, G., Simpson, R. M., 2018. Naturally Occurring Canine Melanoma as a Predictive Comparative Oncology Model for Human Mucosal and Other Triple Wild-Type Melanomas. Int. J. Mol. Sci. 19. https://doi.org/10.3390/ijms19020394

49. Hogge, G. S., Burkholder, J. K., Culp, J., Albertini, M. R., Dubielzig, R. R., Yang, N. S., MacEwen, E. G., 1999. Preclinical development of human granulocyte-macrophage colony-stimulating factor-transfected melanoma cell vaccine using established canine cell lines and normal dogs. Cancer Gene Ther. 6, 26-36. https://doi.org/10.1038/sj.cgt.7700015

50. Huang, B., Lei, Z., Zhao, J., Gong, W., Liu, J., Chen, Z., Liu, Y., Li, D., Yuan, Y., Zhang, G.-M., Feng, Z.-H., 2007. CCL2/CCR2 pathway mediates recruitment of myeloid suppressor cells to cancers. Cancer Lett. 252, 86-92. https://doi.org/10.1016/j.canlet.2006.12.012

51. Ishioka, K., Suzuki, Y., Tajima, K., Ohtaki, S., *Miyabe*, M., Takasaki, M., Mori, A., Momota, Y., Azakami, D., Sako, T., 2013. Monocyte chemoattractant protein-1 in dogs affected with neoplasia or inflammation. J. Vet. Med. Sci. 75, 173-177.

52. Jacobsen, C. N., Aasted, B., Broe, M. K., Petersen, J. L., 1993. Reactivities of 20 anti-human monoclonal antibodies with leucocytes from ten different animal species. Vet. Immunol. Immunopathol. 39, 461-466. https://doi.org/10.1016/0165-2427 (93) 90075-F 53. James, B. R., Anderson, K. G., Brincks, E. L., Kucaba, T. A., Norian, L. A., Masopust, D., Griffith, T. S., 2014. CpG-mediated modulation of MDSC contributes to the efficacy of Ad5-TRAIL therapy against renal cell carcinoma. Cancer Immunol. Immunother. 63, 1213-1227. https://doi.org/10.1007/s00262-014-1598-8

54. Jiang, H., Gebhardt, C., Umansky, L., Beckhove, P., Schulze, T. J., Utikal, J., Umansky, V., 2015. Elevated chronic inflammatory factors and myeloid-derived suppressor cells indicate poor prognosis in advanced melanoma patients. Int. J. Cancer 136, 2352-2360. https://doi.org/10.1002/ijc.29297

55. Jiang, J., Guo, W., Liang, X., 2014. Phenotypes, accumulation, and functions of myeloid-derived suppressor cells and associated treatment strategies in cancer patients. Hum. Immunol. 75, 1128-1137. https://doi.org/10.1016/j.humimm.2014.09.025

56. Jordan, K. R., Amaria, R. N., Ramirez, O., Callihan, E. B., Gao, D., Borakove, M., Manthey, E., Borges, V. F., McCarter, M. D., 2013. Myeloid-derived suppressor cells are associated with disease progression and decreased overall survival in advanced-stage melanoma patients. Cancer Immunol. Immunother. 62, 1711-1722. https://doi.org/10.1007/s00262-013-1475-x 57. Khaled, Y. S., Ammori, B. J., Elkord, E., 2013. Myeloid-derived suppressor cells in cancer: recent progress and prospects. Immunol. Cell Biol. 91, 493-502.

58. Kim, Y. W., Kim, S.-K., Kim, C. S., Kim, I. Y., Cho, M. Y., Kim, N. K., 2014. Association of Serum and Intratumoral Cytokine Profiles with Tumor Stage and Neutrophil Lymphocyte Ratio in Colorectal Cancer. Anticancer Res. 34, 3481-3487.

59. Lana, S., Plaza, S., Hampe, K., Burnett, R., Avery, A. C., 2006. Diagnosis of Mediastinal Masses in Dogs by Flow Cytometry. J. Vet. Intern. Med. 20, 1161-1165. https://doi.org/10.1111/j.1939-1676.2006.tb00716.x 60. Lechner, M. G., Liebertz, D. J., Epstein, A. L., 2010. Characterization of Cytokine-Induced Myeloid-Derived Suppressor Cells from Normal Human Peripheral Blood Mononuclear Cells. J. Immunol. 185, 2273-2284. https://doi.org/10.4049/jimmunol.1000901

61. Lim, S. Y., Yuzhalin, A. E., Gordon-Weeks, A. N., Muschel, R. J., 2016. Targeting the CCL2-CCR2 signaling axis in cancer metastasis. Oncotarget 7, 28697.

62. Lindsay, C. R., Spiliopoulou, P., Waterston, A., 2015. Blinded by the light: why the treatment of metastatic melanoma has created a new paradigm for the management of cancer. Ther. Adv. Med. Oncol. 7, 107-121.

63. MacEwen, E. G., Kurzman, I. D., Vail, D. M., Dubielzig, R. R., Everlith, K., Madewell, B. R., Rodriguez, C. O., Phillips, B., Zwahlen, C. H., Obradovich, J., Rosenthal, R. C., Fox, L. E., Rosenberg, M., Henry, C., Fidel, J., 1999. Adjuvant therapy for melanoma in dogs: results of randomized clinical trials using surgery, liposome-encapsulated muramyl tripeptide, and granulocyte macrophage colony-stimulating factor. Clin. Cancer Res. Off. J. Am. Assoc. Cancer Res. 5, 4249-4258.

64. MacEwen, E. G., Patnaik, A. K., Harvey, H. J., Hayes, A. A., Matus, R., 1986. Canine oral melanoma: comparison of surgery versus surgery plus *Corynebacterium parvum*. Cancer Invest. 4, 397-402.

65. Mandruzzato, S., Brandau, S., Britten, C. M., Bronte, V., Damuzzo, V., Gouttefangeas, C., Maurer, D., Ottensmeier, C., van der Burg, S. H., Welters, M. J. P., Walter, S., 2016. Toward harmonized phenotyping of human myeloid-derived suppressor cells by flow cytometry: results from an interim study. Cancer Immunol. Immunother. 65, 161-169. https://doi.org/10.1007/s00262-015-1782-5

66. Manley, C. A., Leibman, N. F., Wolchok, J. D., Rivière, I. C., Bartido, S., Craft, D. M., Bergman, P. J., 2011. Xenogeneic Murine Tyrosinase DNA Vaccine for Malignant Melanoma of the Digit of Dogs. J. Vet. Intern. Med. 25, 94-99. https://doi.org/10.1111/j.1939-1676.2010.0627.x 67. Marvel, D., Gabrilovich, D. I., 2015. Myeloid-derived suppressor cells in the tumor microenvironment: expect the unexpected. J. Clin. Invest. https://doi.org/10.1172/JCI80005

68. Meyer, C., Cagnon, L., Costa-Nunes, C. M., Baumgaertner, P., Montandon, N., Leyvraz, L., Michielin, O., Romano, E., Speiser, D. E., 2014. Frequencies of circulating MDSC correlate with clinical outcome of melanoma patients treated with ipilimumab. Cancer Immunol. Immunother. 63, 247-257. https://doi.org/10.1007/s00262-013-1508-5

69. Milner, R. J., Salute, M., Crawford, C., Abbot, J. R., Farese, J., 2006. The immune response to disialoganglioside GD3 vaccination in normal dogs: A melanoma surface antigen vaccine. Vet. Immunol. Immunopathol. 114, 273-284. https://doi.org/10.1016/j.vetimm.2006.08.012

70. Mucha, J., Majchrzak, K., Taciak, B., Hellmén, E., Król, M., 2014. MDSCs Mediate Angiogenesis and Predispose Canine Mammary Tumor Cells for Metastasis via IL-28/IL-28RA (IFN-2) Signaling. PLOS ONE 9, e103249. https://doi.org/10.1371/journal.pone.0103249

71. Neel, J. A., Snyder, L., Grindem, C. B., 2012. Thrombocytosis: a retrospective study of 165 dogs. Vet. Clin. Pathol. 41, 216-222. https://doi.org/10.1111/j.1939-165X.2012.00416.x 72. Nikolic Nielsen, L., Kjelgaard-Hansen, M., Kristensen, A. T., 2013. Monocyte chemotactic protein-1 and other inflammatory parameters in Bernese Mountain dogs with disseminated histiocytic sarcoma. Vet. J. 198, 424-428. https://doi.org/10.1016/j.tvjl.2013.07.030

73. O'Neill, K., Guth, A., Biller, B., Elmslie, R., Dow, S., 2009. Changes in Regulatory T Cells in Dogs with Cancer and Associations with Tumor Type. J. Vet. Intern. Med. 23, 875-881. https://doi.org/10.1111/j.1939-1676.2009.0333.x 74. Owen, L . . . , 1980. TNM Classification of Tumours in Domestic Animals.

75. Perry, J. A., Thamm, D. H., Eickhoff, J., Avery, A. C., Dow, S. W., 2011. Increased monocyte chemotactic protein-1 concentration and monocyte count independently associate with a poor prognosis in dogs with lymphoma. Vet. Comp. Oncol. 9, 55-64. https://doi.org/10.1111/j.1476-5829.2010.00235.x 76. Rao, S., Lana, S., Eickhoff, J., Marcus, E., Avery, P. R., Morley, P. S., Avery, A. C., 2011. Class II Major Histocompatibility Complex Expression and Cell Size Independently Predict Survival in Canine B-Cell Lymphoma. J. Vet. Intern. Med. 25, 1097-1105. https://doi.org/10.1111/j.1939-1676.2011.0767.x 77. Rudolph, B. M., Loquai, C., Gerwe, A., Bacher, N., Steinbrink, K., Grabbe, S., Tuettenberg, A., 2014. Increased frequencies of CD11b (+) CD33 (+) CD14 (+) HLA-DR (low) myeloid-derived suppressor cells are an early event in melanoma patients. Exp. Dermatol. 23, 202-204. https://doi.org/10.1111/exd.12336

78. Schiffman, J. D., Breen, M., 2015. Comparative oncology: what dogs and other species can teach us about humans with cancer. Philos. Trans. R. Soc. B Biol. Sci. 370, 20140231. https://doi.org/10.1098/rstb.2014.0231

79. Schilling, B., Sucker, A., Griewank, K., Zhao, F., Weide, B., Görgens, A., Giebel, B., Schadendorf, D., Paschen, A., 2013. Vemurafenib reverses immunosuppression by myeloid derived suppressor cells: Vemurafenib and MDSCs in melanoma. Int. J. Cancer 133, 1653-1663. https://doi.org/10.1002/ijc.28168

80. Schmidt, H., Bastholt, L., Geertsen, P., Christensen, I. J., Larsen, S., Gehl, J., Maase, H. von der, 2005. Elevated neutrophil and monocyte counts in peripheral blood are associated with poor survival in patients with metastatic melanoma: a prognostic model. Br. J. Cancer 93, 273-278. https://doi.org/10.1038/sj.bjc.6602702

81. Sherger, M., Kisseberth, W., London, C., Olivo-Marston, S., Papenfuss, T. L., 2012. Identification of myeloid derived suppressor cells in the peripheral blood of tumor bearing dogs. BMC Vet. Res. 8, 209.

82. Shirota, Y., Shirota, H., Klinman, D. M., 2012. Intratumoral Injection of CpG Oligonucleotides Induces the Differentiation and Reduces the Immunosuppressive Activity of Myeloid-Derived Suppressor Cells. J. Immunol. 188, 1592-1599. https://doi.org/10.4049/jimmunol.1101304

83. Simpson, R. M., Bastian, B. C., Michael, H. T., Webster, J. D., Prasad, M. L., Conway, C. M., Prieto, V. M., Gary, J. M., Goldschmidt, M. H., Esplin, D. G., Smedley, R. C., Piris, A., Meuten, D. J., Kiupel, M., Lee, C.-C. R., Ward, J. M., Dwyer, J. E., Davis, B. J., Anver, M. R., Molinolo, A. A., Hoover, S. B., Rodriguez-Canales, J., Hewitt, S. M., 2014. Sporadic naturally occurring melanoma in dogs as a preclinical model for human melanoma. Pigment Cell Melanoma Res. 27, 37-47. https://doi.org/10.1111/pcmr.12185

84. Smedley, R. C., Spangler, W. L., Esplin, D. G., Kitchell, B. E., Bergman, P. J., Ho, H.-Y., Bergin, I. L., Kiupel, M., 2011. Prognostic Markers for Canine Melanocytic Neoplasms: A Comparative Review of the Literature and Goals for Future Investigation. Vet. Pathol. 48, 54-72. https://doi.org/10.1177/0300985810390717

85. Sottnik, J. 1., Rao, S., Lafferty, M. h., Thamm, D. h., Morley, P. s., Withrow, S. j., Dow, S. w., 2010. Association of Blood Monocyte and Lymphocyte Count and Disease-Free Interval in Dogs with Osteosarcoma. J. Vet. Intern. Med. 24, 1439-1444. https://doi.org/10.1111/j.1939-1676.2010.0591.x 86. Tcyganov, E., Mastio, J., Chen, E., Gabrilovich, D. I., 2018. Plasticity of myeloid-derived suppressor cells in cancer. Curr. Opin. Immunol. 51, 76-82. https://doi.org/10.1016/j.coi.2018.03.009

87. Tikoo, S., Haass, N. K., 2015. Friends or foes: IL-10 and TGF-β in melanoma. Exp. Dermatol. 24, 254-255. https://doi.org/10.1111/exd.12661

88. Tsai, M.-J., Chang, W.-A., Huang, M.-S., Kuo, P.-L., 2014. Tumor Microenvironment: A New Treatment Target for Cancer. ISRN Biochem. 2014, 1-8. https://doi.org/10.1155/2014/351959

89. Vasievich, E. A., Huang, L., 2011. The suppressive tumor microenvironment: a challenge in cancer immunotherapy. Mol. Pharm. 8, 635-641.

90. Vesely, M. D., Kershaw, M. H., Schreiber, R. D., Smyth, M. J., 2011. Natural Innate and Adaptive Immunity to Cancer. Annu. Rev. Immunol. 29, 235-271.
https://doi.org/10.1146/annurev-immunol-031210-101324

91. von Euler, H., Sadeghi, A., Carlsson, B., Rivera, P., Loskog, A., Segall, T., Korsgren, O., Tötterman, T. H., 2008. Efficient adenovector CD40 ligand immunotherapy of canine malignant melanoma. J. Immunother. Hagerstown Md 1997 31, 377-384. https://doi.org/10.1097/CJI.0b013e31816a812d 92. Watanabe, Y., Kano, R., Maruyama, H., Hasegawa, A., Kamata, H., 2010. Small interfering RNA (siRNA) against the Bcl-2 gene increases apoptosis in a canine melanoma cell line. J. Vet. Med. Sci. 72, 383-386.

93. Williams, L. E., Packer, R. A., 2003. Association between lymph node size and metastasis in dogs with oral malignant melanoma: 100 cases (1987-2001). J. Am. Vet. Med. Assoc. 222, 1234-1236.

94. Wong, K., van der Weyden, L., Schott, C. R., Foote, A., Constantino-Casas, F., Smith, S., Dobson, J. M., Murchison, E. P., Wu, H., Yeh, I., Fullen, D. R., Joseph, N., Bastian, B. C., Patel, R. M., Martincorena, I., Robles-Espinoza, C. D., Iyer, V., Kuijjer, M. L., Arends, M. J., Brenn, T., Harms, P. W., Wood, G. A., Adams, D. J., 2019. Cross-species genomic landscape comparison of human mucosal melanoma with canine oral and equine melanoma. Nat. Commun. 10. https://doi.org/10.1038/s41467-018-08081-1

95. Yamauchi, Y., Safi, S., Blattner, C., Rathinasamy, A., Umansky, L., Juenger, S., Warth, A., Eichhorn, M., Muley, T., Herth, F. J. F., Dienemann, H., Platten, M., Beckhove, P., Utikal, J., Hoffmann, H., Umansky, V., 2018. Circulating and Tumor Myeloid-derived Suppressor Cells in Resectable Non-small-cell Lung Cancer. Am. J. Respir. Crit. Care Med. https://doi.org/10.1164/rccm.201708-1707OC 96. Yao, Y., Simard, A. R., Shi, F.-D., Hao, J., 2013. IL-10-Producing Lymphocytes in Inflammatory Disease. Int. Rev. Immunol. 32, 324-336. https://doi.org/10.3109/08830185.2012.762361

97. Yuan, L., Xu, B., Fan, H., Yuan, P., Zhao, P., Suo, Z., 2015. Pre- and post-operative evaluation: percentages of circulating myeloid-derived suppressor cells in rectal cancer patients. Neoplasma 62, 239-249. https://doi.org/10.4149/neo_2015_029

98. Zhang, J., Patel, L., Pienta, K. J., 2010. CC chemokine ligand 2 (CCL2) promotes prostate cancer tumorigenesis and metastasis. Cytokine Growth Factor Rev. 21, 41-48. https://doi.org/10.1016/j.cytogfr.2009.11.009

99. Zhao, Yang, Wu, T., Shao, S., Shi, B., Zhao, Yong, 2016. Phenotype, development, and biological function of myeloid-derived suppressor cells. OncoImmunology 5, e1004983. https://doi.org/10.1080/2162402X.2015.1004983 100. Zoglmeier, C., Bauer, H., Norenberg, D., Wedekind, G., Bittner, P., Sandholzer, N., Rapp, M., Anz, D., Endres, S., Bourquin, C., 2011. CpG Blocks Immunosuppression by Myeloid-Derived Suppressor Cells in Tumor-Bearing Mice. Clin. Cancer Res. 17, 1765-1775. https://doi.org/10.1158/1078-0432.CCR-10-2672

What is claimed is:

1. A vaccine composition consisting of liposomes containing:

an effective amount of disialoganglioside GD3 or GD2, or a combination of GD3 and GD2 to enhance antibody production in a subject; and an effective amount of an adjuvant consisting of monophosphoryl lipid A (MPL); and an effective amount of a CpG oligodeoxynucleotide (CpG-ODNs).

2. The vaccine composition of claim 1, wherein the liposomes comprise a zeta potential of negative 20-10 mV.

3. The vaccine composition of claim 2, wherein the zeta potential is negative 17.32±3.02 mV.

4. A method of treating a cancer in a subject, comprising:

administering to the subject an effective amount of the vaccine composition of claim 1, wherein the vaccine composition is effective to produce antibodies against disialoganglioside GD3, or GD2, or a combination thereof.

5. The method of claim 4, wherein before the administrating step, a cell sample is obtained from the subject, and wherein disialoganglioside GD3 ganglioside, and/or GD2 ganglioside is detected in the cells.

6. The method of claim 4, wherein the administration step occurs in conjunction with a chemotherapy treatment regimen in the subject.

7. The method of claim 6, wherein the administration occurs within 12-240 hours of chemotherapy treatment.

8. The method of claim 4, wherein the administration is intradermal.

9. The method of claim 4, wherein the cancer comprises a brain tumor, a melanoma or a sarcoma.

10. The method of claim 9, wherein the sarcoma comprises an osteosarcoma.

11. A method of producing a GD3 or GD2, or combination of GD3 and GD2-nano-liposome composition, comprising:

obtaining a liposome composition wherein the liposome composition comprises monophosphoryl Lipid A (MPL)-containing liposomes; and combining an effective amount of a disialoganglioside GD3, or GD2, or a combination thereof self-antigen and CpG ODN to the liposome composition.

12. The method of claim 11, wherein the nano-liposome of the liposome composition comprises a mean Zeta-potential of −17.32±3.02 mV.

13. The method of claim 11, wherein the MPL comprises a primary constituent of the liposomes.

14. The method of claim 11, wherein a molar ratio of MPL to liposome is at least 1:3.

15. The method of claim 11, wherein the liposome composition is produced by combining amounts of Lipid A, squalene, lecithin, Tween 80 and water to form a mixture; and sonicating the mixture for a time sufficient to form an emulsion.

16. The method of claim 15, further comprising combining the liposome composition with GD3 or GD2, or a combination thereof, and/or CPG-ODN after 24-48 hours post sonication.

* * * * *